United States Patent
Wasson et al.

(10) Patent No.: US 10,201,295 B2
(45) Date of Patent: Feb. 12, 2019

(54) USER INTERACTIONS FOR A BANDAGE TYPE MONITORING DEVICE

(71) Applicant: Verily Life Sciences LLC, Mountain View, CA (US)

(72) Inventors: Jaclyn Leverett Wasson, Berkeley, CA (US); Zenghe Liu, Alameda, CA (US); Brian Otis, Saratoga, CA (US); William James Biederman, Berkeley, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 802 days.

(21) Appl. No.: 14/657,909

(22) Filed: Mar. 13, 2015

(65) Prior Publication Data
US 2016/0262670 A1  Sep. 15, 2016

(51) Int. Cl.
*A61B 5/145*   (2006.01)
*A61B 5/01*    (2006.01)
(Continued)

(52) U.S. Cl.
CPC ........ *A61B 5/14503* (2013.01); *A61B 5/0022* (2013.01); *A61B 5/01* (2013.01);
(Continued)

(58) Field of Classification Search
CPC .............. A61B 5/1455; A61B 5/14551; A61B 5/14552; A61B 5/14553; A61B 5/14532;
(Continued)

(56) References Cited

U.S. PATENT DOCUMENTS

| 6,069,552 A * | 5/2000 | Van Zeeland ......... G06F 3/0338 |
| | | 200/512 |
| 6,700,086 B2 * | 3/2004 | Serizawa ............. H01H 13/702 |
| | | 200/512 |

(Continued)

FOREIGN PATENT DOCUMENTS

WO   2014159229 A1   10/2014
WO   2015/017712      2/2015

OTHER PUBLICATIONS

International Search Report and Written Opinion for International Application No. PCT/US2016/020249 dated May 6, 2016.
(Continued)

*Primary Examiner* — Eric Winakur
*Assistant Examiner* — Chu Chuan (JJ) Liu
(74) *Attorney, Agent, or Firm* — McDonnell Boehnen Hulbert & Berghoff LLP

(57) ABSTRACT

A body-mountable device includes a flexible substrate configured for mounting to a skin surface. The device includes an input component configured to receive inputs from a user, e.g., finger presses, swipes, motions of the sensing platform, or gestures. Received inputs could include calibration data, for example, known values of a sensed property to compare with corresponding values obtained by a sensor of the device. The device can additionally include an output component configured to provide outputs to a user. Outputs could include indications of sensor readings, medical alerts, or operational states of the device. The flexible substrate of the device is configured to be adhered or otherwise mounted to the skin in a manner that minimally impacts activities of the body.

21 Claims, 6 Drawing Sheets

(51) Int. Cl.
*A61B 5/024* (2006.01)
*A61B 5/11* (2006.01)
*A61B 5/00* (2006.01)
*A61B 5/1486* (2006.01)
*A61B 5/15* (2006.01)

(52) U.S. Cl.
CPC ............ *A61B 5/02438* (2013.01); *A61B 5/11* (2013.01); *A61B 5/1451* (2013.01); *A61B 5/14532* (2013.01); *A61B 5/6801* (2013.01); *A61B 5/6823* (2013.01); *A61B 5/6824* (2013.01); *A61B 5/6833* (2013.01); *A61B 5/6843* (2013.01); *A61B 5/742* (2013.01); *A61B 5/7405* (2013.01); *A61B 5/7455* (2013.01); *A61B 5/0002* (2013.01); *A61B 5/1125* (2013.01); *A61B 5/14865* (2013.01); *A61B 5/150022* (2013.01); *A61B 5/150969* (2013.01); *A61B 2560/0412* (2013.01); *A61B 2562/164* (2013.01)

(58) Field of Classification Search
CPC ... A61B 5/0059; A61B 5/1459; A61B 5/1468; A61B 5/01; A61B 5/11; A61B 5/14503; A61B 5/02438; A61B 5/1451; A61B 5/6801; A61B 5/6843; A61B 5/7455; A61B 5/7405; A61B 5/0022; A61B 5/6833; A61B 5/742; A61B 5/0002; A61B 5/1125; A61B 5/0205; A61B 5/14865; A61B 5/6823; A61B 5/6824
See application file for complete search history.

(56) References Cited

U.S. PATENT DOCUMENTS

| | | | |
|---|---|---|---|
| 7,949,382 B2 | 5/2011 | Jina | |
| 8,202,697 B2 | 6/2012 | Holmes | |
| 8,512,245 B2 | 8/2013 | Markle et al. | |
| 2002/0019022 A1 | 2/2002 | Dunn et al. | |
| 2003/0100040 A1* | 5/2003 | Bonnecaze | A61B 5/0031 435/14 |
| 2003/0122794 A1* | 7/2003 | Caldwell | A47B 57/00 345/173 |
| 2006/0250354 A1* | 11/2006 | Takata | G06F 3/0202 345/156 |
| 2007/0100218 A1 | 5/2007 | Sweitzer et al. | |
| 2008/0091090 A1* | 4/2008 | Guillory | A61B 5/0478 600/301 |
| 2009/0002199 A1* | 1/2009 | Lainonen | G06F 3/0414 341/20 |
| 2010/0234706 A1* | 9/2010 | Gilland | A61B 5/14552 600/344 |
| 2010/0256456 A1 | 10/2010 | Natarajan | |
| 2012/0238834 A1* | 9/2012 | Hornick | A61B 5/02416 600/301 |
| 2012/0296187 A1 | 11/2012 | Henning et al. | |
| 2013/0041235 A1 | 2/2013 | Rogers et al. | |
| 2014/0180137 A1 | 6/2014 | Stivoric et al. | |
| 2014/0275899 A1 | 9/2014 | Gottlieb et al. | |
| 2014/0378777 A1 | 12/2014 | Conrad et al. | |
| 2015/0005589 A1 | 1/2015 | Bly et al. | |
| 2015/0018639 A1 | 1/2015 | Stafford | |

OTHER PUBLICATIONS

Getting starting with Guardian REAL-Time Continuous Glucose Monitoring, product guide, 2009, Medtronic, Northridge, CA.
Guardian REAL-Time Continuous Glucose Monitoring System, User Guide, 2006, Medtronic MiniMed, Northridge, CA.
Dexcom G4 Platinum Professional Continuous Glucose Monitoring System, User's Guide, 2014, Dexcom, Inc.
Dexcom G4 Platinum Continuous Glucose Monitoring System, Quick Start Guide, 2013, Dexcom, Inc., San Diego, CA.
Jonah Comstock, "Medtronic showcases smartphone-enabled continuous glucose monitoring," MobiHealthNews, http://mobihealthnews.com, Sep. 24, 2014.

* cited by examiner

USER INTERACTIONS FOR A BANDAGE TYPE MONITORING DEVICE

BACKGROUND

Unless otherwise indicated herein, the materials described in this section are not prior art to the claims in this application and are not admitted to be prior art by inclusion in this section.

Certain medical conditions or states can be characterized by slow changes of a physiological property (e.g., a blood glucose concentration) over long periods of time and/or by infrequent, short-timescale events. Such physiological properties can be measured periodically (e.g., by periodically accessing blood of a person). Additionally or alternatively, an implanted or wearable device could be employed to provide continuous or near-continuous measurement of such physiological properties. Such implantable or wearable devices can be battery powered and/or powered by radio frequency energy or other wireless energy sources. Further, such devices can be configured to indicate measured physiological properties wirelessly (e.g., by using an RFID antenna and transmitter, by using a Bluetooth antenna and transmitter).

SUMMARY

Some embodiments of the present disclosure provide a body-mountable device including: (i) a sensor configured to detect a physiological property; (ii) an input component; and (v) one or more electronic components configured to: (a) use the sensor to obtain data related to the physiological property, (b) use the input component to receive an input, and (c) perform one or more actions based on the received input.

Some embodiments of the present disclosure provide a body-mountable device including: (i) sensor means configured to detect a physiological property; (ii) input means; and (iii) controller means configured to: (a) use the sensor means to obtain data related to the physiological property, (b) use the input means to receive an input, and (c) perform one or more actions based on the received input.

Some embodiments of the present disclosure provide a method including operating a body-mountable device mounted to a skin surface, where the body-mountable device includes: (a) a sensor configured to detect a physiological property; (b) one or more electronic components; and (c) an input component; wherein the operating includes: (i) obtaining, by the one more electronic components, data related to the physiological property using the sensor; (ii) receiving, by the one more electronic components, an input via the input component; and (iii) performing, by the one more electronic components, one or more actions based on the received input.

These as well as other aspects, advantages, and alternatives, will become apparent to those of ordinary skill in the art by reading the following detailed description, with reference where appropriate to the accompanying drawings.

DETAILED DESCRIPTION

Figure 1A:
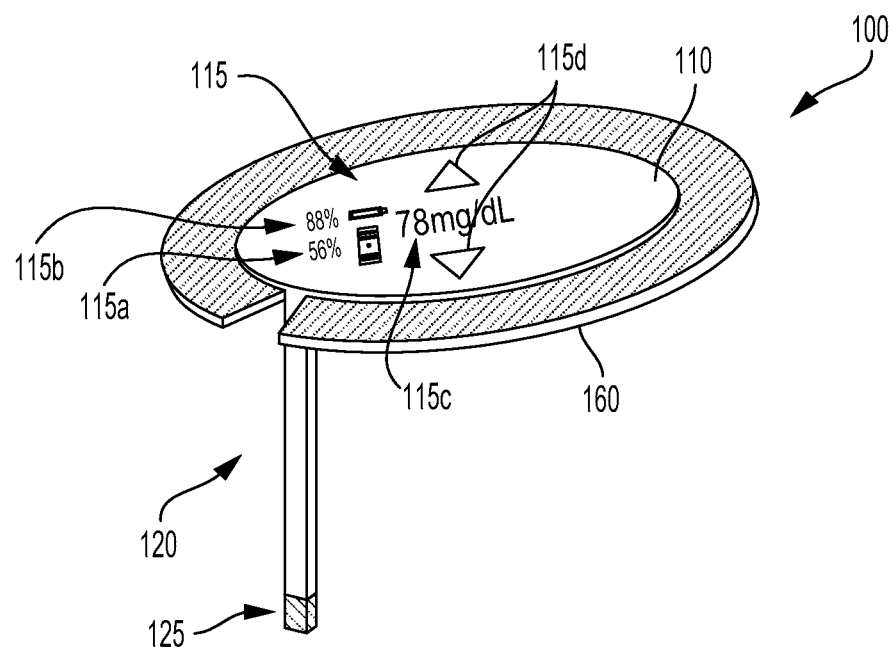
FIG. 1A is a top aspect view of an example body-mountable device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Some embodiments of the present disclosure provide a body-mountable device configured to be mounted to a skin surface of a living body (e.g., to skin of the upper arm or abdomen of a person), with one or more sensors for quantitatively and qualitatively detecting one or more physiological properties (e.g., a heart rate, a temperature, a concentration of glucose or some other analyte in interstitial fluid or some other fluid) of the living body in real-time. Such a body-mountable device further includes a user interface configured to receive inputs from a user (e.g., a user to whose body the device is mounted) and/or to present outputs to the user to provide some application(s) of the body-mountable device. Further, elements of the body-mountable device are disposed on a flexible substrate that is configured to be mounted to the skin surface (e.g., by use of glue, tape, dry adhesive, or other adhesive means). The flexibility of the flexible substrate (and of the body-mountable device overall) could provide a sensing platform that minimally interferes with activities of a body to which the sensing platform is mounted and/or that can be mounted to a body comfortably for protracted periods of time. This could include the flexible substrate and/or the sensing platform being sufficiently flexible that the flexible substrate complies with the shape of the skin surface and deforms with changes in the shape of the skin surface. Those of skill in the art will recognize that the sensing platform described herein may be provided in devices that could be mounted on a variety of portions of the human body to measure a variety of physiological properties of the human body (e.g., concentrations of a variety of analytes in a variety of fluids of the body, temperature, galvanic properties, ECG, muscle activity). Those of skill in the art will also recognize that the sensing platform described herein may be provided in devices that could be mounted in locations other than locations on a human body, e.g., locations on an animal body, locations that are part of a natural or artificial environment.

A user interface of a sensing platform as described herein could provide a variety of functions and applications of the sensing platform. In some examples, the user interface could provide means for changing or setting an operational state of the sensing device and/or for causing the performance of some function by the sensing platform. For example, the user interface could provide means for a user to cause the sensing platform to perform a measurement of the physiological property using the sensor, to set the sensing platform into a sleep or other low-power state, to set a rate of operation of the sensor to detect the physiological property, or to control some other aspect of operation or function of the sensing platform. In some examples, the user interface could provide means for inputting calibration or other data to the sensing platform, e.g., for inputting calibration data related to the operation of the sensor to detect the physiological property. Additionally or alternatively, the user interface could provide means for inputting information about the state of a user of the sensing platform, e.g., to indicate a physical or mental state of the user, to indicate an activity of the user, to indicate that the user has eaten a meal or taken a drug, or to indicate some other information. The user interface could provide means for providing an indication of information to a user, for example, information about the operation of the sensing platform (e.g., battery charge state, an amount of free memory), detected physiological properties (e.g., a glucose level detected using the sensor), or some other information available to the sensing platform.

An input component of a sensing platform could be configured to detect a variety of inputs by detecting a variety of physical properties of the sensing platform and/or of the environment of the sensing platform. The input component could be configured to detect sound (e.g., voice commands), motion of the device (e.g., a gesture that includes motion of the skin surface to which the sensing platform is mounted), contact between the sensing platform and a finger or other portion of a user's body, or some other inputs. For example, the input component could be configured to detect a location, motion, pressure, gesture, or other information about objects (e.g., a finger or other body part) near the sensing platform. The input component could include a capacitive touch sensor configured to detect a single touch, multiple touches, gestures, swipes, or other inputs. The input component could be and/or include a flexible component (e.g., a capacitive touch sensor comprising one or more electrodes composed of one or more layers or sheets of a flexible conductive material and one or more sheets of a flexible nonconductive material). In some examples, the input component could include one or more elements in common with the sensor. For example, the sensor of the sensing platform could be configured to detect a temperature of the skin surface to which the sensing platform is mounted; additionally, the temperature sensor could be used to detect inputs (e.g., contact between the sensing platform and a finger or other object) by detecting changes over time in the temperature detected using the temperature sensor.

An output component of a sensing platform could be configured to provide a variety of different types of information via a variety of means. The output component could provide an indication related to an operational status of the sensing platform (e.g., to provide an indication related to the battery charge state or free memory space of the device, to provide an indication related to an operating mode or state of the device) and/or related to the physiological property detected using the sensor (e.g., to provide an indication related to a glucose level detected using the sensor). The output component could be used to provide an indication related to a course of action that a user could take (e.g., to administer a drug, to seek medical assistance). The output component could be used to provide an indication related to an alert generated by the sensing platform (e.g., an alert that a measured physiological property is outside of some specified limits, and alert that a user is experiencing or is about to experience an adverse health state). The output component could include light-emitting elements (e.g., LEDs, OLEDs, displays), color-changing elements (e.g., e-ink elements or displays, LCDs), haptic elements (e.g., vibrators, buzzers, electrohaptic elements), acoustical elements (e.g., buzzers, speakers), or some other elements configured to provide an indication of some information, e.g., to a user. The output component could include flexible elements, e.g., the output component could include a flexible OLED display.

The sensing platform could include a variety of sensors configured to detect a variety of physiological properties and/or properties of the environment of the sensing platform. In some examples, the sensor could include an analyte sensor configured to detect an analyte (e.g., glucose) in a fluid on or within the skin surface to which the sensing platform is mounted (e.g., interstitial fluid within or beneath the skin) In such examples, the sensor could include two or more electrodes configured to detect the analyte electrochemically (e.g., potentiometrically or amperometrically), optically (e.g., by illuminating and/or detecting light emitted from an analyte-sensitive substance that has an optical property related to the analyte), or by some other means. One or more sensors could detect a temperature on or within the skin. One or more sensors could be configured to detect an electrical or magnetic field, an electrical potential between two points on or within the skin (e.g., to detect an electromyogram, to detect an electrocardiogram, to detect a galvanic skin potential), an electrical conductivity between two or more points on or within the skin (e.g., to detect a galvanic skin response, to detect a skin conductance), or some other electrical and/or magnetic property or variable on or within the skin and/or in the environment of the sensing platform. One or more sensors could be configured to detect and/or emit light, e.g., to illuminate and/or detect light emitted from on or within the skin (e.g., to photoplethysmographically detect a flow of blood within the skin and/or to detect a timing and/or rate of heartbeats), to detect ambient light received by the sensing platform (e.g., to detect the presence, motion, or other properties of a finger or other body part proximate the sensing platform, e.g., to receive an input from a user). Additional or alternative sensors detecting additional or alternative properties or variables are anticipated.

The sensor could be disposed on a sensor probe that is configured to penetrate the skin (e.g., to a specified depth within the skin) such that the sensor can measure an analyte in a fluid within the skin. Such a sensor probe could be configured to penetrate to a specified depth within the skin (e.g., to a depth within the dermis, to a subcutaneous depth)

such that at least one sensor disposed on the sensor probe can measure an analyte in fluid (e.g., interstitial fluid) at the specified depth. The sensor probe could be flexible or rigid; in some examples, the sensor probe could comprise an elongate extension of the flexible substrate material. The sensor probe could be configured to pierce the skin (e.g., could be sufficiently rigid and/or sharpened such that the sensor probe can be driven into the skin). Additionally or alternatively, the sensor probe could be configured to pierce and/or penetrate the skin in combination with an insertion device. For example, the sensor probe could be configured to be mounted within the channel of a half-needle or to some other means for piercing the skin; the half needle or other piercing means could be used to pierce the skin and to subsequently retract, leaving the sensor probe in place penetrating the skin. One or more sensors could be disposed at the end of such a sensor probe and/or at one or more additional locations along the length of such a sensor probe.

A sensing platform can include a power source, electronics, and an antenna all disposed on the flexible substrate configured to be mounted to skin of a living body. The electronics can operate one or more sensors (e.g., a sensor disposed at the distal end of a sensor probe) to perform measurements of an analyte (e.g., to measure the concentration of the analyte in interstitial fluid within or beneath the skin). The electronics could additionally operate the antenna to wirelessly communicate the measurements from the sensor or other information to an external reader or some other remote system via the antenna. One or more of the power source, antenna, electronics, or other components of the sensing platform could be flexible; for example, the power source could include a thin, flexible lithium ion battery. In some examples, one or more of the power source, antenna, electronics, or other components of the sensing platform could be sufficiently flexible to allow for flexibility of the overall sensing platform and/or of elements of the sensing platform that are able to be mounted to skin (e.g., to provide greater comfort and/or to minimize effect on user activities when mounted to skin of a user).

Batteries of a sensing platform as described herein could be single-use or could be rechargeable. Rechargeable batteries could be recharged by power provided by radio frequency energy harvested from an antenna disposed on the flexible substrate. The antenna can be arranged as a loop of conductive material with leads connected to the electronics. In some embodiments, such a loop antenna can also wirelessly communicate the information (e.g., measurements of the analyte made using a sensor of the sensing platform) to an external reader (e.g., to a cellphone) by modifying the impedance of the loop antenna so as to modify backscatter radiation from the antenna. Additionally or alternatively, the sensing platform could include a chip, dipole, or other type of antenna for transmitting and/or reflecting RF energy to indicate information to an external reader. Further, such antennas could be used to transfer additional information, e.g., to indicate a temperature, light level, or other information detected by the sensing platform, to receive commands or programming from an external device, or to provide some other functionality.

It should be understood that the above embodiments, and other embodiments described herein, are provided for explanatory purposes, and are not intended to be limiting.

II. Example Flexible Biosensor Platform

Figure 1B:
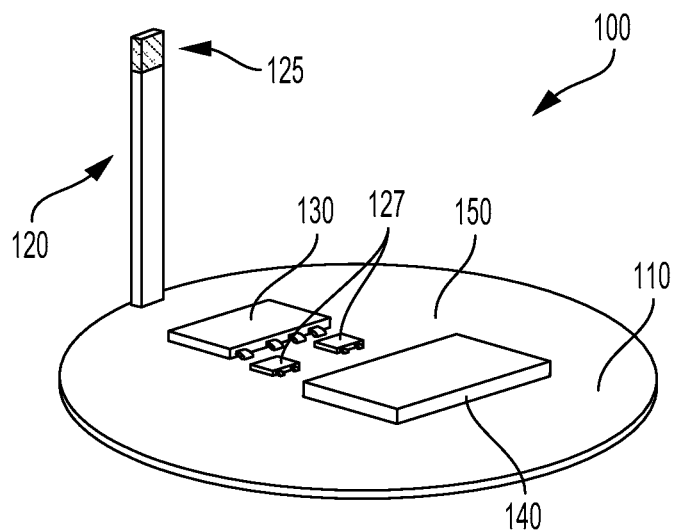
FIG. 1B is a bottom aspect view of the example body-mountable device shown in FIG. 1A.

FIG. 1A is a top view of an example body-mountable sensing platform 100. FIG. 1B is a bottom view of the example body-mountable sensing platform shown in FIG. 1A. It is noted that relative dimensions in FIGS. 1A and 1B are not necessarily to scale, but have been rendered for purposes of explanation only in describing the arrangement of the example body-mountable sensing platform 100. The body-mountable device 100 is formed of a flexible substrate 110 shaped (as an illustrative example) as a circular disk. A user interface 115 is disposed on the flexible substrate 110 and is configured to provide an indication of information visually, acoustically, haptically, or by some other means (e.g., to display a charge status of the sensing platform, to visually provide an indication of a value of a property measured by the sensing platform, to emit a sound, to vibrate, to provide an electro-haptic stimulus, or to provide some other indication of an alert state determined by the sensing platform 100) and to receive inputs from a user (e.g., to detect a user pressing one or more points on the device (e.g., the illustrated arrows), to detect gestures or motions of a user). A sensor probe 120 extends from the flexible substrate 110 and is configured to penetrate a skin surface (e.g., to penetrate into skin of the upper arm or abdomen of a human body). An analyte sensor 125 is disposed at a distal end of the sensor probe 120. The analyte sensor 125 is configured to detect an analyte (e.g., glucose) in interstitial or other fluids under and/or within the skin when the sensor probe 120 penetrates the skin. An optical sensor 127 is also included to optically detect one or more properties of skin (e.g., by illuminating and/or detecting light emitted from the skin to detect an optical property, e.g., a color, reflectivity, or other properties). An adhesive layer 160 is provided to mount the flexible substrate 110 to a skin surface (the adhesive layer 160 is not shown in FIG. 1B, to allow illustration of elements of the body-mountable sensing platform 100 that are disposed on the bottom surface 150 of the flexible substrate 110).

The body-mountable sensing platform 100 additionally includes electronics 130 disposed on the flexible substrate 110 and configured to provide various applications of the sensing platform 100 including, e.g., operating the analyte sensor 125 to detect an analyte, operating the optical sensor 127 to detect and optical property of skin, operating some other sensor of the sensing platform 100 to detect some other property or variable, receiving inputs from a user (e.g., using the user interface 115), providing an indication of information to a user (e.g., using the user interface 115), recording information (e.g., user inputs, measured concentrations of the analyte) in a memory of the electronics 130, and communicating information (e.g., by using an antenna to wirelessly indicate such information) to an external system. The antenna (not shown) could be configured as a loop antenna on bottom surface 150 (e.g., encircling electronics 130), or the antenna could be configured as a chip antenna or some other configuration. A battery 140 is provided to power the body-mountable sensing platform 100 (e.g., to power the electronics 130). Components (e.g., antennas, batteries, electronics, user interface elements) could additionally or alternatively be disposed on the top surface of the flexible substrate 110 (i.e., the surface of the flexible substrate 110 opposite the bottom surface 150).

The flexible substrate 110 is configured to be mounted to a skin surface. In the example shown in FIGS. 1A and 1B, this includes a layer of adhesive 160 being provided to adhere the flexible substrate 110 to a skin surface. Additional or alternative means could be provided to mount the flexible substrate 110 to a skin surface. For example, a liquid or gel adhesive could be applied to the skin surface and/or to the flexible substrate 110 to mount the flexible substrate 110 to the skin surface. The flexible substrate 110 could be placed on the skin surface and secured using tape or other adhesives. In some examples, the body-mountable sensing platform 100 could include a dry adhesive configured to removably mount the flexible substrate 110 to a skin surface. Other means for mounting the flexible substrate 110 or other elements of the body-mountable sensing platform 100 to a skin surface or to other elements or aspects of a living body are anticipated. Further, in some embodiments, a body-mountable sensing platform 100 could be provided that is configured to be placed proximate a target fluid (e.g., interstitial fluid, synovial fluid, blood, tears, saliva, mucus) without mounting to a skin surface or other tissue surface. For example, a body-mountable sensing platform 100 as described herein could be configured to be placed between the teeth and cheek of a living body, on the eye of a living body, or at some other location of a living body without being mounted to a particular tissue surface.

The flexible substrate 110 and/or elements of the body-mountable sensing platform 100 disposed thereon can have a thickness, shape, composition, rigidity, compliance, elasticity, viscoelasticity, and/or other properties specified such that the flexible substrate 110 can be mounted to a skin surface of a living body and further such that such mounting minimally interferes with activities of the living body (e.g., motions of the living body). This could include the flexible substrate 110 being sufficiently flexible that mounting of the flexible substrate 110 to the skin surface causes a minimum of discomfort. The body-mountable sensing platform 100 could be sufficiently flexible that the flexible substrate 110 and components mounted thereto/dispose therein comply with the shape of the skin surface and deform with changes in the shape of the skin surface This could include elements disposed on/in the flexible substrate 110 being flexible. For example, elements (e.g., electronic components, input components, output components, sensors) could include or be composed of flexible polymers, flexible metal films, traces, and/or electrodes (e.g., metal traces or electrodes formed on the flexible substrate 110), or other flexible materials and/or materials formed to be flexible (e.g., a rigid material formed to include a strain relief, to be thin or narrow, or otherwise formed such that an element composed of the rigid material is functionally flexible).

Additionally or alternatively, rigid components (e.g., rigid electronic components) could be mounted to the flexible substrate 110 such that the body-mountable sensing platform 100 is, overall, flexible. This could include the rigid components being small, the rigid components being separated by a specified distance on the flexible substrate 110, the rigid components having a long shape and being disposed parallel to each other on the flexible substrate 110 such that the body-mountable sensing platform 100 is flexible in a direction perpendicular to the orientation of the rigid components, or some other configuration of the flexible substrate 110 and components disposed thereon/therein such that the body-mountable sensing platform 100 is flexible (e.g., such that the body-mountable sensing platform 100 is complaint and deforms according to deformations of the skin surface to which that body-mountable sensing platform 100 is mounted, such that the body-mountable sensing platform 100 being mounted to the skin surface minimally interferes with activities of a body/causes minimal discomfort).

The flexible substrate 110 could be composed of polyimide or some other flexible polymeric or other material. The flexible substrate could have a thickness less than approximately 100 microns. Further, the flexible substrate 110 could have a size specified to minimally interfere with activities of the living body. For example, the flexible substrate 110 could have size (e.g., a diameter of a circular portion, as illustrated in FIGS. 1A and 1B) less than approximately 11 millimeters. Diameter and thickness values are provided for explanatory purposes only. Further, the shape of the flexible substrate 110 could be different from that illustrated in FIGS. 1A and 1B or elsewhere herein; for example, the flexible substrate 110 could have an elongate shape, a square or rectangular shape, or some other shape according to an application. For example, the flexible substrate 110 could have an elongate shape to provide sufficient area for disposition of electronics, batteries, user interface components (e.g., touch sensor electrodes, flexible display elements), antennas, or other components on the flexible substrate 110 while minimally impeding motion and/or deformation of the skin surface to which the flexible substrate 110 is mounted (e.g., by being formed and/or mounted to the skin surface such the orientation of the elongate shape of the flexible substrate 110 is perpendicular to a direction of strain of the skin surface).

One or more surfaces of the flexible substrate 110 (e.g., the bottom surface 150) could be used as a platform for mounting electronics such as chips (e.g., via flip-chip mounting) and for patterning conductive materials (e.g., via deposition techniques) to form electrodes, antenna(e), and/or connections. The composition of the flexible substrate 110 could be chosen to allow for the formation and/or disposition of such elements of the body-mountable sensing platform 100. For example, the flexible substrate 110 could be composed of polyimide or some other polymeric and/or metallic material(s) such that metal contacts, traces, and interconnects can be patterned directly on the surface of the flexible substrate 110 (e.g., by sputtering, CVD, or some other deposition process) and/or on a coating or layer formed on one or more surfaces of the flexible substrate 110. Further, such patterned structures and/or other elements disposed on the flexible substrate 110 (e.g., electronics 130, optical sensor 127, battery 140, antennas) could, in combination with the flexible substrate 110, have a thickness or other property specified to provide the overall body-mountable sensing platform 100 with flexibility. For example, the flexible substrate 110 in combination with electronics 130, user interface 115, optical sensor 127, and battery 140 disposed thereon could have a thickness less than approximately 0.5 millimeters.

One or more components of a sensor, input component, output component, or other elements of the body-mountable sensing platform 100 could be formed directly on the flexible substrate 110 as a deposited metal film, dielectric material or coating, or other deposited material. For example, one or more electrodes of a capacitive touch sensor (e.g., a sensor configured to detect the presence, location, motion, or other properties of a fingertip, other body part, or other objects proximate and/or in contact with the capacitive touch sensor) could be formed on the flexible substrate 110 to provide a flexible input component (i.e., the capacitive touch sensor). Electrodes or other elements of a resistive touch sensor, a conductive touch sensor, a pressure sensor that could be operated to receive inputs from a user, an electrohaptic output component (e.g., two or more electrodes configured to be in contact with skin when the body-mountable sensing platform 100 is mounted to the skin and to deliver an electro-haptic stimulus to the skin through the two or more electrodes), an electrochemical analyte sensor, a galvanic skin resistance or potential sensor, an electromyogram (EMG) or electrocardiogram (ECG) sensor, or some other components could be formed by depositing metals or other materials on the flexible substrate 110. Further, organic LED light-emitting elements (e.g., individual OLED indicator lights, OLED displays) or other flexible semiconductors could be deposited and/or formed on or within the flexible substrate 110. Additionally or alternatively, such elements (or other components of a body-mountable sensing platform 100) could be formed separately from the flexible substrate 110 and deposited and/or disposed on the flexible substrate 110 (e.g., using an adhesive, by welding, by reflow soldering between contacts of the element(s) and corresponding metallic pads or traces formed on the flexible substrate 110).

The user interface 115 includes means for receiving inputs (e.g., for detecting the presence of, location of, force exerted on the user interface 115 by, and/or motion of a fingertip or other boy part of a user) and for provide an indication of outputs (e.g., information indicative of the operation of the body-mountable sensing platform 100 and/or sensor results detected by the body-mountable sensing platform 100). In the illustrated example, the user interface 115 includes a flexible touchscreen interface comprising a flexible display (e.g., a flexible array of organic light-emitting diode (OLED) elements) and one or more electrodes or other touch-, capacitive-, and/or pressure-sensitive elements for detecting presses of a finger or other object against the user interface 115 (e.g., to present an input to the user interface 115 to, e.g., change a setting of the device 100). As illustrated, the user interface 115 is being operated to illustrate a battery charge status 115a (e.g., of the flexible battery 140), a memory status of a memory 115b (e.g., of the electronics 130), and an analyte concentration 115c (detected using, e.g., the analyte sensor 125). The user interface 115 additionally presents two arrows 115d indicating regions of the user interface 115 that a user could press or otherwise interact with to present an input to the device 100, e.g., to change an operational state of the device, to change a setting or operational parameter (e.g., calibration data) of the device 100, or to effect some other function of the device. For example, the device 100 could use the user interface 115 to detect one or more finger presses or other user inputs to receive a calibration value for the analyte sensor 125. The arrows 115d and/or other visual elements of the user interface 115 could be static (e.g., printed or otherwise marked on the user interface 115 and/or on the flexible substrate 110) or could be changeable, e.g., by being generated by a display or other output component.

Note that the illustrated user interface 115 is intended as a non-limiting example embodiment. A user interface could be configured differently and/or include different or additional means for indicating information and/or for receiving inputs. For example, a user interface could include speakers, piezo elements, or acoustical elements or other means for generating sounds to indicate information (e.g., to beep, to generate a tone, to play a recorded and/or synthesized sound). A user interface could include a vibrator, one or more electrodes configured to deliver an electro-haptic stimulus to skin, a heating element configured to heat skin, or some other haptic elements configured to deliver a haptic stimulus to a person. A user interface could include one or more electrodes, ultrasonic transducers, cameras, or other means configured to receive inputs by detecting a capacitance, a resistance, a conductance, or some other property related to the location, motion, and/or contact of a finger, body part, or other object proximate to or in contact with the user interface. A user interface could receive input by including one or more pressure sensitive elements configured to detect contact, pressure, force, or other properties of an interaction between the user interface and a finger, body part, or other object in contact with the user interface. A user interface could include a microphone or other pressure transducing element configured to receive inputs by detecting sounds (e.g., vocal commands) produced by a user. A user interface could include additional or alternative input and output components to those described herein.

Inputs received by the user interface 115 could include the detected presence of, location of, contact with, pressure applied by, motion of, a gesture performed by, or other properties of a body part or other object proximate to and/or in contact with the user interface 115 (e.g., proximate to and/or in contact with an input component of the user interface 115). Received inputs could include a location, pressure, duration, or other properties of a body part or other object being in contact with the user interface 115. Received inputs could include a direction of motion of a body part or some other gesture performed by the body part (e.g., upward, downward, or other motion relative to one or more elements of the user interface 115, a clockwise or counter-clockwise motion relative to a capacitive touch sensor of the user interface 115, e.g., around a periphery of the user interface 115). Received inputs could represent selection and/or operation of an element of the user interface (e.g., a 'button' of the user interface, an operational mode from a presented list of operational modes, an element representing an increment or decrement of a value) by a user. Received inputs could indicate a user's intent to change a value of a parameter of the device 100 (e.g., an upward motion could indicate the user's intent to increase a parameter, while a downward motion could indicate the user's intent to decrease the parameters), to change an operational mode of the device 100, or to affect some other operation of the device 110 and/or to indicate some other information (e.g., to indicate an emotional or physical state of a user, to indicate an activity performed by the user).

The user interface 115 could include a variety of input components configured to receive inputs. Such input components could be configured to detect a variety of properties related of the device 100 (e.g., a temperature of the device, an effective capacitance of elements and/or regions of the device 100), of the environment of the device (e.g., a temperature of the environment of the device and/or skin to which the device 100 is mounted, an amount of light received by the device 100), and/or of objects (e.g., fingers) proximate the device 100. In some examples, the input component could include an accelerometer configured to detect the velocity, acceleration, or other properties of motion of the device 100 (e.g., to detect gestures or other inputs performed by a user by performing a motion of a body part to which the device 100 is mounted). In some examples, the input component could include one or more electrodes configured to detect a capacitance related to the presence, location, motion, or other properties of fingers, body parts, or other objects proximate the inputs component. The input component could include multiple such electrodes configured to detect the presence or other properties of body parts or other objects proximate the multiple electrodes, e.g., to detect interaction with (e.g., a finger pressing) a user interface 115 element corresponding to one of the multiple electrodes. For example, the user interface 115 could include a set of electrodes configured to act as a set of capacitive 'buttons' of the user interface. Alternatively, an input component could be configured to detect a pressure (e.g., a pressure exerted on the user interface 115 by a finger or other object), an amount of received light (e.g., an amount of ambient light received by a portion of the user interface 115 that is reduced due to occlusion by a finger or other object), a conductance between two or more electrodes (e.g., a conductance between two electrodes that is reduced due to the presence of a conductive finger or other object between the two electrodes), or some other property related to a received input.

An input component of the body-mountable sensing platform 100 could include a microphone configured to detect sounds in the environment of the device 100. Such sounds could include commands (e.g., spoken words) generated by a user of the device 100. In such examples, the device 100 could be configured to interpret the detected sounds (e.g., by voice recognition) to determine the commands. Additionally or alternatively, the device 100 could record sounds (e.g., speech). Such recorded sounds could be used to determine some information about the user (e.g., to determine an emotional and/or physical state of the user at one or more points in time) or for some other purpose (e.g., to record notes, reminders, or other information spoken by the user).

In some examples, the input component could include one or more elements in common with a sensor of the body-mountable sensing platform 100. For example, a sensor of the device 100 could be configured to detect a temperature of skin to which the device 100 is mounted. Such a sensor could additionally be operated to receive inputs by detecting changes in the detected temperature (e.g., changes in the temperature of the skin and/or the temperature of the device 100) related to contact between a finger or other object and the device (e.g., due to an insulating effect of the presence of the finger or other object). In another example, a sensor of the device 100 could be configured to detect a conductance of skin to which the device 100 is mounted (e.g., by detecting a conductance between two electrodes in contact with the skin). Such a sensor could additionally be operated to receive inputs by detecting changes in the detected conductance related to pressure and/or forces exerted on the device 100 by a finger or other object (e.g., due an increase in the detected conductance related to improved electrical contact between electrodes of the sensor and the skin to which the device 100 is mounted related to the pressure and/or force exerted by the finger or other object).

Inputs received by one or more input components of the user interface 115 could be received and/or detected by the body-mountable sensing platform 100 (e.g., by the electronics 130 operating the user interface 115) and used to perform a variety of functions of the device 100. In some examples, an operational state of the device 100 (e.g., a sleep state, a data-logging state, a data-upload state) could be changed based on one or more received inputs. Providing an indication of information using the user interface 115 (e.g., using an OLED display or other output component(s) of the user interface 115) could be based on one or more received inputs. For example, a type of information indicated (e.g., battery charge status, free memory amount, a value of a detected property) could be based on received inputs. Further, such information could be indicated responsive to a received input. For example, a display of the user interface 115 could be deactivated or otherwise placed in a low-power state until an input is received, at which time the display could be operated to indicate some information (e.g., a backlight could be activated, one or more OLED elements of a display could be lit). Received inputs could indicate some information about a user and/or activities of a user and/or the environment of the user. For example, received inputs could correspond to an emotional or physical state of a user (e.g., nausea, malaise), activities of a user (e.g., that the user has performed exercise, consumed a meal, or received and/or taken a drug), or some other information. In some examples, received inputs could indicate one or more parameters that could be used by the device 100. For example, received inputs could represent a calibration value of a property detected by one or more sensors of the device 100 e.g., a blood glucose level detected using some other device. Such a received calibration value could be used to modify the operation of the device 100, e.g., to determine a value of glucose in the blood based on a measured value detected by the analyte sensor 125.

The user interface 115 could include a variety of output components configured to provide an indication of information. As illustrated in FIG. 1A, outputs provided by one or more output components of a body-mountable sensing platform could indicate information about the body-mountable sensing platform (e.g., a battery charge status, an amount of free memory of the device) and/or information detected by the device (e.g., a concentration of an analyte or value of some other property sensed by one or more sensors of the device). Additionally, the output components could provide an indication of means by which a user could indicate inputs or commands to the device. As shown in FIG. 1A, the user interface 115 includes arrows indicating regions of the user interface 115 that a user could interact with (e.g., touch or press) to indicate some input and/or command (e.g., to change a calibration value of a sensor (e.g., 125), to change an operational mode of the device 100). Such indications (e.g., arrows) could be generated by an output component of a device (e.g., by a display, by a light-emitting element) and/or could be static indications printed, embossed, inscribed, or otherwise formed on the user interface 115, flexible substrate 110, or other elements of the device 100. Further, an output component could be configured to provide an indication of information by emitting sounds, by presenting a haptic stimulus to a user (e.g., a vibration, an electrical stimulus, an increased or decreased temperature), or by some other method. Provided indications could additionally include alerts generated by the device 100, e.g., alerts based on a determination that a user is experiencing an adverse health condition (e.g., determined based on a property detected using sensors 125, 127 of the device 100). In some examples, an output component could be operated to indicate information in response to a received input (e.g., a display could be operated to provide an indication of information in response to a received input), in response to a determined alert condition (e.g., an alert sound could be indicated in response to a determination that a user requires medical intervention), or in response to some other event or input (e.g., an alert generated by a remote system in communication with the body-mountable sensing platform 100).

Output components of a body-mountable sensing platform 100 can include a display configured to provide an indication related to a variety of information that is available to the body-mountable sensing platform 100. Such a display could include OLED, LED, liquid crystal, e-ink, or other components and/or displays configured to emit a light, change a color, or otherwise visually indicate some information. In some examples, a body-mountable sensing platform 100 could include one or more discrete light emitters (e.g., LEDs, OLEDs) configured to emit light to indicate some information (e.g., to indicate an alert, to indicate a battery status, to indicate some information related to a property detected by sensors, e.g., 125, 127, of the device 100). Additionally or alternatively, a device 100 could include a piezo element, a speaker, or some other element configured to emit a sound (e.g., to beep, to play an alert sounds, to play a recorded message). In some examples, a body-mountable sensing platform could include a haptic element configured to provide an indication of some information by delivering a haptic stimulus (e.g., vibration, heat, pain, touch) to a user. Such a haptic element could include a vibrator (e.g., a motor configured to drive an unbalanced mass), a piezo element configured to couple vibrations into skin, two or more electrodes configured to deliver an electro-haptic stimulus into skin, or some other components configured to deliver a haptic stimulus to a user.

The electronics 130 disposed on the flexible substrate 110 could include a variety of devices. For example, the electronics 130 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 110. Further, antennas, electrodes, capacitors, resistors, or other components could be formed from such traces or other interconnects formed on the surface of the flexible substrate 110. The electronics 130 can include logic elements configured to operate the analyte sensor 125 to detect an analyte, the optical sensor 127 to detect an optical property of skin, the user interface 115 to receive an input and/or to indicate some information, an antenna (e.g., a loop, dipole, or other type of antenna formed on the flexible substrate 110, a chip antenna disposed on the flexible substrate 110) to wirelessly indicate information (e.g., concentration levels about a detected analyte), and/or to provide other functions. A loop, dipole, or other type of antenna can be one or more layers of conductive material patterned on a surface (e.g., 150) of the flexible substrate 110 to form one or more specified conductive shapes (e.g., a ring, a spiral, a curved or straight line, an elliptical or rectangular patch, a fractal). Electrical interconnects (e.g., traces), antennas, and/or conductive electrodes (e.g., for an electrochemical analyte sensor, for a capacitive touch sensor of an input component, etc.) can be formed from conductive materials patterned on the flexible substrate 110 by a process for precisely patterning such materials, such as deposition, lithography, etc. The conductive materials patterned on the flexible substrate 110 can be, for example, gold, platinum, palladium, titanium, carbon, aluminum, copper, silver, silver-chloride, conductors formed from noble materials, metals, combinations of these, etc.

The sensor probe 120 is an elongate element of the body-mountable sensing platform 100 that is configured to penetrate a skin surface such that the analyte sensor 125 located at the distal end of the sensor probe 120 is in contact with a fluid (e.g., interstitial fluid, blood) containing an analyte of interest (e.g., glucose) when the sensor probe 120 is penetrating the skin. For example, the sensor probe 120 could be more than approximately 2 millimeters long. The sensor probe 120 could have a length or other properties specified such that, when the sensor probe 120 penetrates skin and/or the flexible substrate 120 is mounted to a skin surface, a sensor (e.g., 125) or other element(s) disposed on the sensor probe 120 contact tissue at a specified depth within the skin (e.g., tissue of the dermis of the skin, subcutaneous tissue). For example, the sensor probe 120 could have a length between approximately 500 microns and approximately 6000 microns. Further, the sensor probe 120 could have one or more dimensions specified to provide sufficient area for electrodes or other elements disposed on the sensor probe 120, to minimally interfere with the skin (e.g., by requiring a minimal incision or other alteration of the skin to provide for penetration of the sensor probe 120), or according to some other application. For example, the sensor probe 120 could have a width between approximately 25 microns and approximately 400 microns.

The sensor probe 120 could be composed of a variety of materials and elements formed by a variety of processes. The sensor probe 120 could be composed of a flexible material (e.g., polyimide) or a relatively inflexible material; further, a thickness, width, shape, or other properties of the sensor probe 120 could be specified to provide a degree of flexibility or inflexibility. For example, a flexible sensor probe 120 could have a width between approximately 25 microns and approximately 400 microns and/or a thickness less than approximately 100 microns. In some examples, the sensor probe 120 could be formed from the same material as the flexible substrate 110; i.e., the sensor probe 120 could be an elongate portion of the flexible substrate 110 that extends from a portion of the flexible substrate 110 that is configured to be mounted to a skin surface and/or on which electronics 130 or other components are disposed. Alternatively, the sensor probe 120 could be attached to the flexible substrate 110. For example, the sensor probe 120 could include optical fiber(s), flexible element(s) (e.g., an elongate piece of polyimide or other polymeric or metallic substance), wire(s), elongate pieces of shaped silicon, or other elements adhered, welded, bonded, or otherwise attached to the flexible substrate 110.

Alternatively, such sensor probes could be used for other applications and/or in combination with components or devices other than a flexible substrate (e.g., 110) as described herein. For example, one or more sensors or other elements disposed on the sensor probe 120 could be used as part of an input component configured to receive inputs (e.g., one or more electrodes configured to detect a galvanic skin conductance, an EMG signal, or some other property related to a user input) and/or an output component configured to provide an indication of information (e.g., one or more electrodes configured to deliver an electro-haptic stimulus, a heater configured to deliver heat into skin to indicate some information or alert). Further, note that a body-mountable sensing platform as described herein could lack such a sensor probe, or could include more than one sensor probe.

The sensor probe 120 could be configured to pierce skin to allow the sensor probe 120 to penetrate the skin and dispose the analyte sensor 125 and/or other elements disposed on the sensor probe 120 in contact with interstitial or other fluids within the skin. For example, the sensor probe 120 could be sharpened, could include one or more rigid materials to facilitate application of force to the sensor probe 120 to pierce the skin (e.g., stainless steel tubes, rods, sheets, and/or needles), or could be otherwise configured to pierce skin. In some examples, the sensor probe 120 could include materials having a stiffness or some other property that changes to allow the sensor probe 120 to be used to pierce the skin during a first period of time and subsequently to become less rigid or to change some other property according to an application. In some examples, the sensor probe 120 could include a material configured to initially have a high rigidity, to allow for piercing of skin, and to soften when the sensor probe penetrates the skin for a period of time. For example, the sensor probe 120 could include a piece of poly-2-hydroxyethyl methacrylate (poly-HEMA) or some other hydrogel configured to soften by absorbing water (e.g., from interstitial fluid) once the sensor probe 120 has penetrated the skin. In another example, the sensor probe 120 could include a stiff material that is configured to dissolve into and/or be absorbed by the skin (e.g., polylactic acid (PLA)). Additionally or alternatively, the sensor probe 120 could be inserted into skin by another device that is configured to pierce the skin, or into an incision into the skin formed by another device. For example, the sensor probe 120 could be configured to be mounted within the channel of a half-needle of a device (e.g., a device configured to insert the sensor probe 120 into skin and/or to mount the flexible substrate 110 to a skin surface) such that the half-needle could pierce the skin and subsequently be retracted, leaving the sensor probe 120 in place penetrating the skin.

Note that the depiction of a body-mountable sensor platform 100 having a single sensor probe 120 on a distal end of which a single analyte sensor 125 is disposed and having an optical sensor 127 disposed on a bottom surface 150 of a flexible substrate 110 is intended as a non-limiting, illustrative example. A particular body-mountable sensing platform could include additional sensors disposed at different locations of the sensing platform (e.g., particular locations on a sensor probe). For example, a particular sensor probe of a body-mountable sensor platform could include a plurality of sensors disposed along the length of the particular sensor probe to allow for detection of some property of skin (e.g., a concentration of an analyte within the skin) at a variety of depths within the skin. A body-mountable sensor platform could include more than one sensor probe and such sensor probes could have respective widths, lengths, thicknesses, sensors, sensor locations, or other properties. Further, a body-mountable sensing platform could include sensors that are not disposed at a distal end or other locations on a sensor probe. For example, one or more sensors could be disposed on a flexible substrate (e.g., optical sensor 127 disposed on the bottom surface 150 of the flexible substrate 110) or other element(s) of such a body-mountable sensing platform.

A variety of sensor probes configured to penetrate skin, and devices (e.g., body-mountable sensing platforms) including such sensor probes, are described herein. Such sensor probes could be configured and/or operated to penetrate skin through a pre-existing cut, puncture, incision, or other entry through the surface of the skin into tissue (e.g., dermal tissue, subcutaneous tissue) containing an analyte-containing fluid of interest (e.g., interstitial fluid). Such a pre-existing entry could be formed for the purpose of inserting the sensor probe by a lancet, needle, or other instrument configured to pierce the skin. Additionally or alternatively, the sensor probe and/or some other element of a body-mountable sensing platform could be configured to pierce the skin, e.g., by including rigid elements, by including a sharpened end, or by being configured in some other way to allow piercing of the skin. In some examples, the sensor probe (and body-mountable sensing platform, in embodiments wherein the sensor probe is an element of such a sensing platform) could be removably mounted to an insertion device configured to pierce the skin in combination with the sensor probe and to retract leaving the sensor probe in place (i.e., penetrating the skin).

Figure 2B:
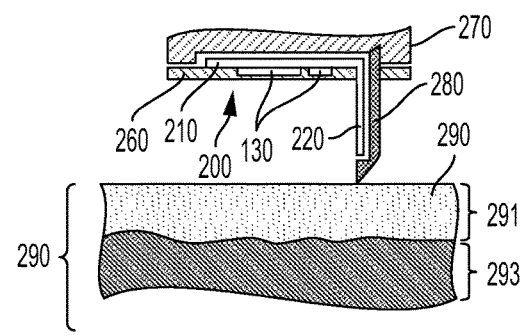
FIG. 2B is a cross-sectional view of the body-mountable device and insertion device of FIG. 2A, positioned proximate to skin of a living body.
Figure 2A:
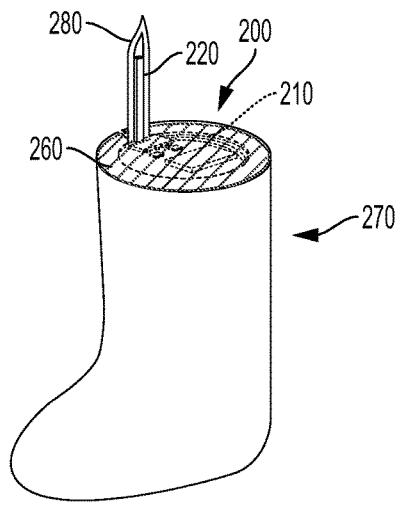
FIG. 2A is an aspect view of an example body-mountable device removably mounted to an example insertion device.

FIG. 2A illustrates an example body-mountable sensing platform 200 removably mounted to an example insertion device 270. The body-mountable sensing platform 200 includes a flexible substrate 210, a sensor probe 220 attached to the flexible substrate 210, and an adhesive layer 260 configured to adhere the flexible substrate 210 to a skin surface. The sensor probe 220 is configured to penetrate the skin and includes a sensor (not shown) disposed on the sensor probe 220 and configured to detect a property of the skin and/or to otherwise interact with tissues beneath and/or within the skin. For example, the sensor could be configured to detect an analyte (e.g., to measure a concentration of glucose) in a fluid within the skin (e.g., in interstitial fluid) when the sensor probe 220 penetrates the skin. The sensor probe 220 is coupled to a needle 280 of the insertion device 270. The needle 280 is a half-needle; that is, the needle 280 includes a channel along the length of the needle 280 in which the sensor probe 220 is disposed. The needle 280 is configured to pierce skin such that the needle 280 and the coupled sensor probe 220 penetrate the skin. That is, the needle is sufficiently rigid and/or has an end that is sufficiently sharp that force can be applied to the insertion device 270 such that the needle 280 pierces the skin. The insertion device 270 can then be moved away from the skin, retracting the needle 280 while the sensor probe 220 remains inserted in (i.e., penetrating) the skin and the flexible substrate 210 remains mounted on the skin surface.

Figure 2C:
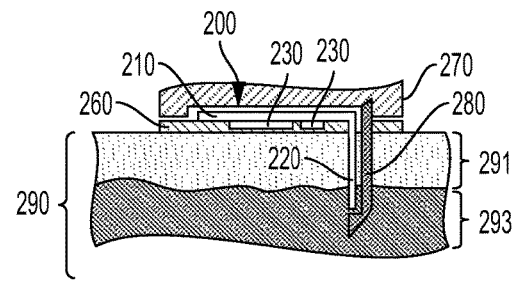
FIG. 2C is a cross-sectional view of the body-mountable device, insertion device, and skin of a living body of FIG. 2B, showing the body-mountable device and insertion device penetrating the skin.
Figure 2D:
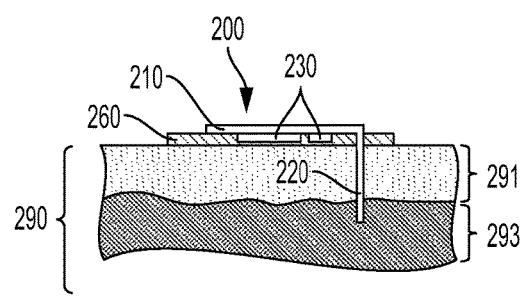
FIG. 2D is a cross-sectional view of the body-mountable device, insertion device, and skin of a living body of FIG. 2B, showing the body-mountable device penetrating the skin and the insertion device retracted from the skin.

FIGS. 2B-2D show, in cross-section, the process of using the insertion device 270 to pierce skin 290. The skin 290 includes an epidermal layer 291 and a dermal layer 293. FIG. 2B shows the body-mountable sensing platform 200 removably mounted to the insertion device 270 such that the sensor probe 220 of the sensing platform 200 is coupled to the needle 280 of the insertion device (that is, in this example, that the sensor probe 220 is disposed within a channel of the needle 280). As shown in FIG. 2B, the insertion device 270 and sensing platform 200 removably mounted thereto are disposed proximate the skin 290, but have not yet pierced and/or penetrated the skin 290.

FIG. 2C shows the insertion device 270 and sensing platform 200 after the needle 280 (and sensor probe 220 coupled thereto) has been inserted into the skin 290 (i.e., the needle 280 has pierced the skin). Further, the flexible substrate 210 has been mounted, via the adhesive action of the adhesive layer 260, to the skin 290 surface. The sensor probe 220 penetrates the skin 290 such that the distal end of the sensor probe 220 is located in the dermal layer 293 of the skin 290 (e.g., such that a sensor disposed on the end of the sensor probe 220 could detect an analyte in interstitial or other fluids present in the dermal layer 293). FIG. 2D shows the sensing platform 200 after the needle 280 of the insertion device 270 has been retracted. The sensor probe 220 continues to penetrate the skin 290 such that the distal end of the sensor probe 220 is located in the dermal layer 293 of the skin 290.

Note that the illustrated insertion device 270 and sensing platform 200 and use thereof to pierce and/or penetrate the skin 290, are intended as non-limiting illustrative examples of such devices and methods. An insertion device 270 and/or sensing platform 200 could have different shapes, include different components and/or elements, be configured different, and/or differ in some other way as will be clear to one of skill in the art. For example, the insertion device could consist of a disk to which a half-needle or other penetrating means are attached and to which a body-mountable sensing platform could be removably mounted. In some examples, the insertion device 270 could be configured to provide some additional functionality, e.g., could be configured to receive communications from the sensing platform (e.g., to received information related to the detected analyte), to recharge a sensing platform, to activate a sensing platform, or to provide some other functionality. In some examples, an insertion device could include a driving mechanism (e.g., a spring-loaded mechanism, a servomechanism including one or more solenoids, motors, or other electromechanical actuators) configured to drive a needle (and sensor probe coupled thereto) into skin (e.g., to a specified depth within the skin, at a sufficiently high speed to minimize user discomfort). In some examples, the needle 280 could be retractable into the insertion device 270 for safety.

Note that the mounting of body-mountable sensing platforms to skin surfaces of living bodies, and in some examples the penetration of such skin by sensor probes of sensing platforms, are intended as non-limiting illustrative examples of devices and methods described herein. Such devices and systems could be used to detect other properties of a body and/or of the environment of the devices and systems in some other way. This could include detecting analytes in or other properties of other tissues by penetrating such other tissues with sensor probes and/or mounting flexible substrates to surfaces of such tissues. For example, sensor probes, flexible substrates, and/or sensing platforms as described herein could be used to detect an analyte within a mucosal epithelium (e.g., within the mucosa of a mouth, nose, or other mucosa of a living body). Additionally or alternatively, sensor probes, flexible substrates, and/or sensing platforms as described herein could be used to detect analytes in a variety of fluids without penetrating tissues (e.g., to detect an analyte in a tissue present in a volume of a living body, e.g., to detect an analyte in peritoneal fluid by disposing a sensing-platform as described herein within the peritoneal cavity of a living body). Further, systems and devices as described herein could be used to detect properties of an animal and/or plant body, and/or to detect properties of a natural environment (e.g., a stream, a lake) and/or an artificial environment (e.g., a pharmaceutical process, a water treatment process, a food processing process).

A sensor disposed at a distal end of a sensor probe or at some other location of a body-mountable sensing platform as described herein could include a variety of components and/or substances configured in a variety of ways. In some examples, such sensors could include one or more substances that selectively interact with an analyte. For example, such substances could include proteins, enzymes, aptamers, DNA, RNA, nano-structures, antibodies, reagents, nano-structured surfaces, or other substances configured to selectively bind to, catalyze a reaction of, or otherwise selectively interact with an analyte of interest. Such an analyte-sensitive substance could be disposed on a surface of a sensing platform (e.g., on a metal surface of an electrode, on a surface of an optical fiber, on some other surface of a sensor probe and/or flexible substrate) and/or within a polymer, gel, or other layer that is permeable to the analyte and that is disposed on such a surface.

In some examples, an analyte-selective substance could be disposed on a surface of a sensing platform (e.g., on an electrode surface) by crosslinking the substance on the surface (e.g., using glutaraldehyde to crosslink the analyte-sensitive substance). In some examples, an analyte-selective substance can be disposed within a polymer layer formed on a surface of a sensing platform. Such a polymer layer can be permeable to the analyte and contain a reagent that selectively reacts with the analyte to create a reaction product that can be sensed directly by an electrode and/or by some other element (e.g., a fluorophore or other substance that selectively interacts with the reaction product). In some examples, the polymer layer that contains the analyte-selective substance is a hydrogel that includes 2-hydroxyethyl methacrylate units. Such a hydrogel could contain additional polymer units or other chemicals to adjust a permeability of the hydrogel to the analyte, to bind the analyte-selective substance within the hydrogel, in increase a degree of crosslinking of the hydrogel, or to specify one or more other properties of the hydrogel. For example, such a hydrogel could additionally include di(ethylene glycol) dimethacrylate units.

In some examples, the sensor of a sensing platform can include two or more electrodes configured to detect or measure the analyte electrochemically. The two or more electrodes could include a working electrode selectively sensitive to the analyte and a reference electrode. In some examples, exposing the sensor to a target fluid (e.g., interstitial fluid) causes a potentiometric voltage to develop between the working electrode and the reference electrode that can indicate the concentration of the analyte near the working electrode. Additionally or alternatively, a specified voltage could be applied between the reference electrode and the working electrode and an amount of current that responsively flows through the working electrode could be related to the concentration of the analyte near the working electrode and/or the rate at which the analyte diffuses to the working electrode (e.g., through a hydrogel layer containing an analyte-selective substance and/or through a hydrogel layer disposed to protect the working electrode and/or other components of the sensor).

In some examples, the sensor of a sensing platform can include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. Additionally or alternatively, a color, saturation, absorption spectrum, or some other optical property of a substance disposed at the end of the sensor probe could be related to the presence, concentration, or some other property of the analyte. The sensor platform could include a light emitter and/or a light detector configured to illuminate and to receive light emitted from the analyte-sensitive substance, respectively, in order to determine the optical property of the substance that is related to the analyte. In some examples, a sensor probe of the sensing platform could include an optical fiber and the analyte-selective substance could be disposed on a distal end of such an optical fiber. In such examples, a light emitter and/or a light detector could be disposed at a proximal end of the optical fiber, such that the light emitter and light detector illuminate and received light from the analyte-sensitive substance via the optical fiber. In such examples, the light emitter and/or light detector could be disposed on a flexible substrate of the sensor platform (e.g., as part of electronics disposed on the flexible substrate).

In some examples, a polymer, gel, or other layer that is permeable to the analyte could be disposed over to one or more components of the sensor (e.g., over a working electrode, over a layer containing and/or composed of an analyte-selective substance) and/or other elements of a sensing platform to protect the elements of the sensing platform or according to some other application. In some examples, a permeability, thickness, or other properties of such an analyte-permeable layer (and/or of a similar layer containing an analyte-selective substance) could be specified to control a rate of diffusion of the analyte from interstitial fluid to a sensor (e.g., to a metal electrode surface of the sensor) or to some other element of the sensing platform (e.g., to an analyte-selective substance disposed proximate to an electrode, optical fiber, or some other element of the sensing platform). In some examples, a protective or other polymer layer could be a hydrogel, e.g., a hydrogel that includes units of 2-hydroxethyl methacrylate and/or units of di(ethylene glycol) dimethacrylate.

In some examples, a sensor of a body-mountable sensing platform could be configured to detect an optical property of a tissue and/or of a body to which the sensing platform is mounted. This could include detecting a reflectance, absorbance, fluorescence intensity, fluorescence lifetime, or some other optical properties of tissue. Such detection could include emitting light toward and/or detecting light emitted from a tissue in one or more bands of wavelengths and/or within a plurality of such bands of wavelengths. For example, an optical sensor could be configured to detect a reflectance spectrum, an absorbance spectrum, a fluorescence spectrum, an excitation spectrum, an emission spectrum, or some other spectral information or spectrum relating to optical properties of a tissue. Such an optical sensor could include one or more photodetectors, photodiodes, phototransistors, or other light-detecting elements configured to detect light within one or more bands of wavelengths, within a specified range of polarizations, or having some other specified properties. Such an optical sensor could include one or more LEDs, lasers, or other light-emitting elements configured to emit light within one or more ranges of wavelengths, having a specified polarization, a specified coherence length, a specified angle relative to skin and/or one or more photodetectors, or some other specified property.

Such an optical sensor could detect one or more optical properties related to the presence and/or amount of a substance (e.g., a concentration of hemoglobin in blood, a volume of blood in a portion of skin), a property of a substance (e.g., an oxygenation state of hemoglobin in blood), or some other properties of skin. Such detected properties could be used to determine one or more properties of the skin to which the sensing platform is mounted and/or of a body comprising the skin. For example, an optical sensor could be configured and/or operated to detect an oxygenation of blood in the skin, a timing and/or frequency of pulses of blood in the skin and/or of heartbeats of the heart of the body comprising the skin, a degree of perfusion of the skin, or some other properties.

A body-mountable sensor platform could include additional or alternative sensors. Such sensors could include temperature sensors, accelerometers, gyroscopes, magnetometers, barometric pressure sensors, magnetic field sensors, electric field sensors, electromagnetic field sensors, or other types of sensors. Such sensors could be configured and/or operated to detect properties of skin to which the sensing platform is mounted and/or to detect properties of the environment of the sensing platform. Such sensors could include two or more electrodes configured to detect an electrical potential between and/or an electrical current through the two or more sensors. Such sensors could be configured and/or operated to detect a galvanic skin conductance, a galvanic skin potential, an electromyogram, an electrocardiogram, or some other electrophysiological property of skin to which the sensing platform is mounted and/or of a body comprising the skin. A body-mountable sensing platform could include additional or alternative sensors and/or combinations thereof.

III. Example Electronics of a Flexible Biosensor Platform

Figure 3:
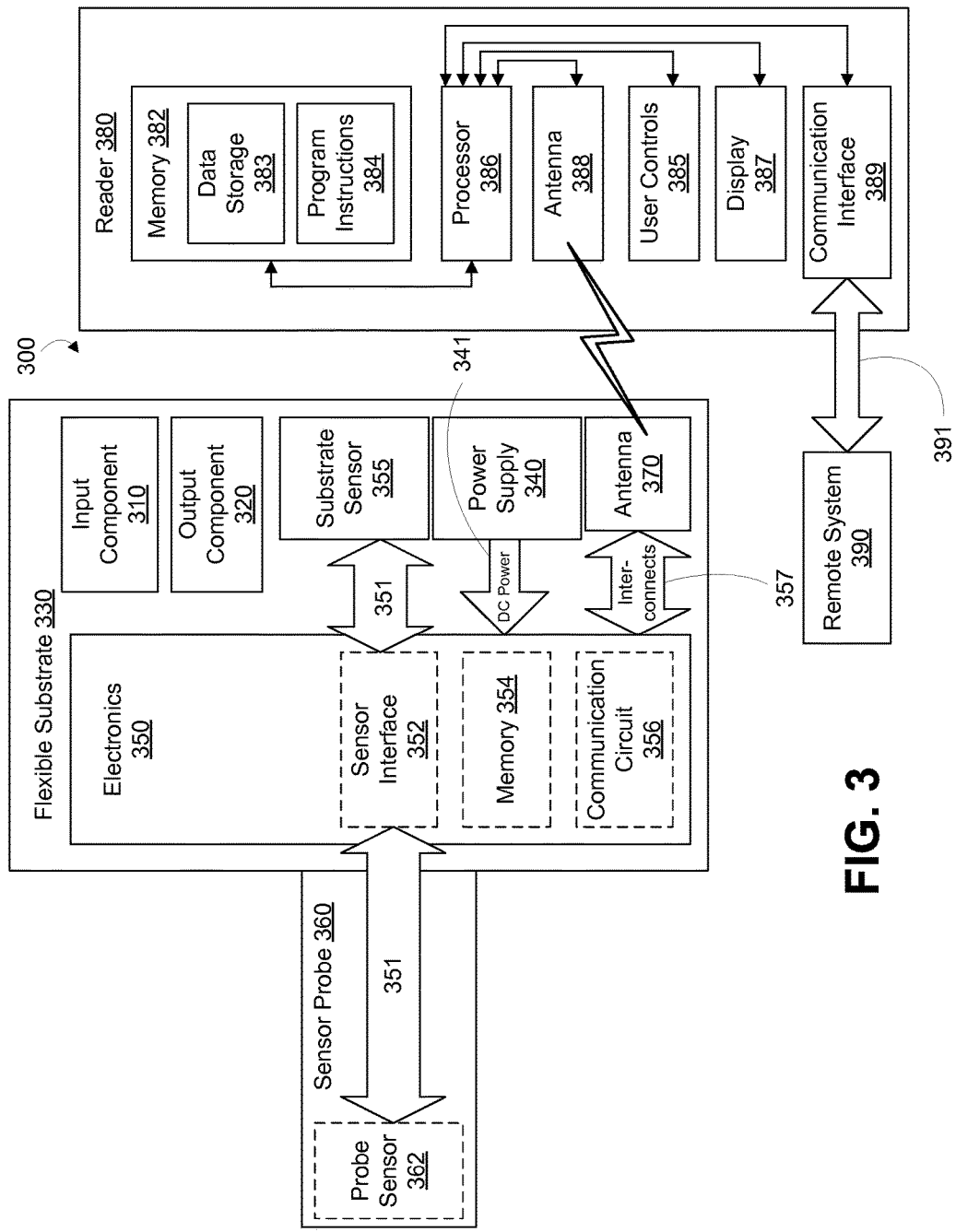
FIG. 3 is a block diagram of an example system that includes a body-mountable device in wireless communication with an external reader.

FIG. 3 is a block diagram of a system that includes a body-mountable sensor platform 300 in wireless communication with an external reader 380. The body-mountable sensor platform 300 includes a flexible substrate 330 that is made of a flexible polymeric or metallic material formed to be mounted to a skin surface. The flexible substrate 330 provides a mounting surface for a power supply 340, electronics 350, input component 310 and output component 320 of a user interface, substrate sensor 355, and a communication antenna 370. The power supply 340 supplies operating voltages to the electronics 350 and/or other elements of the sensing platform 300. The antenna 370 is operated by the electronics 350 to communicate information to and/or from the body-mountable sensing platform 300. The antenna 370, the electronics 350, user interface 355, and the power supply 340 can all be situated on the flexible substrate 330.

The flexible substrate 330 and/or elements of the body-mountable sensing platform 100 disposed thereon can have a thickness, shape, composition, rigidity, compliance, elasticity, viscoelasticity, and/or other properties specified such that the flexible substrate 330 can be mounted to a skin surface of a living body and further such that such mounting minimally interferes with activities of the living body (e.g., motions of the living body). This could include the flexible substrate 330 being sufficiently flexible that mounting of the flexible substrate 330 to the skin surface causes a minimum of discomfort. The flexible substrate 330 could be composed of polyimide or some other flexible polymeric or other material. One or more surfaces of the flexible substrate 330 could be used as a platform for mounting components or elements of the antenna 370, the electronics 350, user interface 355, and the power supply 340 such as chips (e.g., via flip-chip mounting) and conductive materials (e.g., via deposition techniques) that form electrodes, antenna(e), and/or connections. The composition of the flexible substrate 330 could be specified such that metal contacts, traces, and interconnects can be patterned directly on the surface of the flexible substrate 330 (e.g., by sputtering, CVD, or some other deposition process) and/or on a coating or layer formed on one or more surfaces of the flexible substrate 330. The body-mountable sensor platform 300 could be sufficiently flexible that the flexible substrate 330 and components mounted thereto/dispose therein comply with the shape of the skin surface and deform with changes in the shape of the skin surface. This could include elements disposed on/in the flexible substrate 330 being flexible. For example, elements (e.g., electronics 350, input components 310, output components 320, substrate sensor 355) could include or be composed of flexible polymers, flexible metal films, traces, and/or electrodes (e.g., metal traces or electrodes formed on the flexible substrate 330), or other flexible materials and/or materials formed to be flexible (e.g., a rigid material formed to include a strain relief, to be thin or narrow, or otherwise formed such that an element composed of the rigid material is functionally flexible).

The electronics 350 disposed on the flexible substrate 330 could include a variety of devices. For example, the electronics 350 could include an antenna (e.g., a chip antenna), a microcontroller, amplifiers, light emitters, light detectors, temperature sensors, transmitters, radios, transceivers, or some other component or components. Such components can be mounted to and/or electrically connected via interconnects or traces patterned on the flexible substrate 330. Further, antennas, electrodes, capacitors, resistors, or other components could be formed from such traces or other interconnects formed on the surface of the flexible substrate 330. The electronics 350 can include logic elements configured to operate the sensors 362, 355 to detect a property (e.g., an analyte in a body), an antenna (e.g., a loop, dipole, or other type of antenna formed on the flexible substrate 330, or a chip antenna disposed on the flexible substrate 330) to wirelessly indicate information (e.g., concentration levels) about the detected analyte, an electrode of a capacitive touch sensor to receive an input, and/or to provide other functions. Electrical interconnects (e.g., traces), antennas, and/or conductive electrodes (e.g., for an electrochemical analyte sensor, etc.) can be formed from conductive materials patterned on the flexible substrate 330 by a process for precisely patterning such materials, such as deposition, lithography, etc. The conductive materials patterned on the flexible substrate 330 can be, for example, gold, platinum, palladium, titanium, carbon, aluminum, copper, silver, silver-chloride, conductors formed from noble materials, metals, combinations of these, etc.

The body-mountable sensing platform 300 further includes a sensor probe 360 that is attached to the flexible substrate 330. The sensor probe 360 is an elongate element of the body-mountable sensing platform 300 that is configured to penetrate a skin surface such that a probe sensor 362 located at a distal end of the sensor probe 360 is in disposed within skin (e.g., in contact with interstitial fluid, blood, or some other fluid of interest) when the sensor probe 360 is penetrating the skin. That is, the sensor probe 360 is configured to extend beneath the skin surface into an epidermal, dermal, or subcutaneous tissue of a body that includes the skin surface. The sensor probe 360 could be composed of a flexible material (e.g., polyimide) or a relatively inflexible material; further, a thickness, width, shape, or other properties of the sensor probe 360 could be specified to provide a degree of flexibility or inflexibility. In some examples, the sensor probe 360 could be formed from the same material as the flexible substrate 330; i.e., the sensor probe 360 could be an elongate portion of the flexible substrate 330 that extends from a portion of the flexible substrate 330 that is configured to be mounted to a skin surface and/or on which electronics 350 or other components are disposed. Alternatively, the sensor probe 360 could be attached to the flexible substrate 330. For example, the sensor probe 360 could include optical fiber(s), wire(s), elongate pieces of shaped silicon, patterned conductive traces, or other elements adhered, welded, bonded, or otherwise attached to the flexible substrate 330. Alternatively, such sensor probes could be used for other applications and/or in combination with components or devices other than a flexible substrate (e.g., 330) as described herein.

The substrate 330 includes one or more surfaces suitable for mounting the electronics 350 (including a sensor interface 352, a memory 354, and a communication circuit 356), the power supply 340, the input component 310, the output component 320, the substrate sensor 355, and the antenna 370. The flexible substrate 330 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. For example, the antenna 370 can be formed by depositing a pattern of gold or another conductive material on the flexible substrate 330. Similarly, interconnects 341, 351, 357 between the electronics 350 and the power supply 340, between the sensor interface 352 and the sensor 362, and between the communication circuit 356 and the antenna 370, and/or other interconnects between components of the device 300, can be formed by depositing suitable patterns of conductive materials on the substrate 330. A combination of microfabrication techniques including, without limitation, the use of photoresists, masks, deposition techniques and/or plating techniques can be employed to pattern materials on the substrate 330. The substrate 330 can be a material, such as polyimide, polyethylene terephthalate ("PET"), parylene, or another material sufficient to structurally support the circuitry and/or electronics.

The power supply 340 is configured to provide energy to power the electronics 350. For example, the power supply 340 could include a battery. Such a battery could be flexible, e.g., the battery could be a flexible lithium-ion battery or some other type of flexible battery. The battery could be flexible to allow the flexible substrate 330 to which the battery is mounted to flex in response to deformation and/or motion of a skin surface to which the flexible substrate 330 is mounted. Such flexibility could be provided to increase the comfort of a living body to which the sensing platform 300 is mounted and/or to minimally interfere with motions and/or activities of such a living body. A battery (or combination of batteries provided as part of the power supply 340) could have a capacity sufficient to power the device for a protracted period of time, e.g., 18 hours, a week, or some other protracted period of time of periodic operation of the sensor 362, antenna 370, and memory 354 to detect an analyte, to record information related to the analyte in the memory 354, and to wirelessly communicate such detected information to the external reader 380. For example, the battery could be a flexible battery with a capacity of more than approximately 60 microamp-hours and a thickness of less than approximately 0.5 millimeters.

In some examples, the power supply 340 could include a rechargeable battery and could further include some means for recharging such a battery. For example, the power supply 340 could include contacts disposed on a surface of the flexible substrate 330 and configured to receive electrical power from complimentary contacts of a charging device (e.g., the external reader 380). In another example, the sensing platform 300 could include a loop antenna (e.g., a loop antenna comprising conductive traces patterned on the flexible substrate 330) and the power supply 340 could be configured to use the loop antenna to receive RF energy from an external device (e.g., the external reader 380); in some examples, such an RF-energy-receiving antenna could be the same antenna as the antenna 370 used to communicate with external devices.

The input component 310 and output component 320 are configured to receive inputs from a user (e.g., a user to whose body the device is mounted) and to provide an indication of information to the user, respectively, to provide some application(s) of the sensing platform 300. Such user-interface elements (e.g., displays, sensors, buttons) could be flexible and/or mounted to and/or formed on (e.g., flexible electrodes of a capacitive touch sensor and/or electro-haptic stimulator) the flexible substrate 330 of the sensing platform 300. In some examples, the input component 310 could provide means for changing or setting an operational state or operational parameter of the sensing platform 300 and/or for causing the performance of some function by the sensing platform 300.

For example, the input component 310 could provide means for a user to cause the sensing platform 300 to perform a measurement of a physiological property using one or both of the sensors 362, 355, to set the sensing platform 300 into a sleep or other low-power state, to set a rate of operation of one or both of the sensors 355, 362 to detect the physiological property, to operate the output component 320 to provide some indication (e.g., to provide an indication related to data measured using one of the sensors 355, 362), or to control some other aspect of operation or function of the sensing platform 300. In some examples, the input component 310 could provide means for inputting calibration or other data to the sensing platform 300, e.g., for inputting calibration data related to the operation of the sensors 355, 362 to detect the physiological property. Additionally or alternatively, the input component 310 could provide means for inputting information about the state of a user of the sensing platform 300, e.g., to indicate a physical or mental state of the user, to indicate an activity of the user, to indicate that the user has eaten a meal or taken a drug, or to indicate some other information.

The input component 310 could be configured to receive inputs related to communication between the body-mountable sensing platform 300 and an external system (e.g., 380). For example, the body-mountable sensing platform 300 could be configured to communicate information related to a measurement made by the sensor(s) 355, 362 (e.g., using the communication circuit 356 and antenna 370) in response to a received input. The communicated information could include stored information (e.g., analyte concentration values detected using the probe sensor 362 at a plurality of past points in time and stored in the memory 354); additionally or alternatively, the communicated information could include information obtained using the sensor(s) 355, 362 in response to the received input. In some examples, the communicated information could include information related to an information link between the body-mountable sensing platform 300 and the external system (e.g., 380). For example, the communicated information could include a request for further communication and/or a request for information about a communications protocol (e.g., the communicated information could include information related to linking the body-mountable sensing platform 300 with the external system, e.g., related to performing a Bluetooth pairing between the body-mountable sensing platform 300 and the external system). Further, the communicated information could include security information (e.g., cryptographic keys, passwords) related to securing further communication between the body-mountable sensing platform 300 and the external system.

The output component 320 could provide means for indicating information to a user, for example, information about the operation of the sensing platform 300 (e.g., battery charge state, an amount of free memory), detected physiological properties (e.g., a blood glucose level detected using the probe sensor 362, a heart rate and/or blood oxygenation detected photoplethysmographically using the substrate sensor 355), or some other information available to the sensing platform 300.

The input component 310 could be configured to receive a variety of inputs by detecting a variety of physical variables. The input component 310 could be configured to detect sound (e.g., voice commands), motions of the sensing platform 300 (e.g., a gesture that includes motion of the skin surface to which the sensing platform is mounted), contact between the sensing platform 300 and a finger or other portion of a user's body, the presence, location, motion, or other properties of a finger or other object proximate the input component 310, or some other inputs. For example, the input component 310 could be configured to detect a location, motion, pressure, gesture, or other information about objects (e.g., a finger or other body part) proximate the sensing platform 300. The input component 310 could include a capacitive touch sensor configured to detect a single touch, multiple touches, gestures, swipes, or other inputs. The input component 310 could include flexible components. In some examples, the input component 310 could include one or more elements in common with one or both of the sensors 355, 362. For example, the substrate sensor 355 of the sensing platform 300 could be configured to detect a temperature of the skin surface to which the sensing platform 300 is mounted; additionally, the substrate sensor 355 could be used to detect inputs (e.g., contact between the sensing platform 300 and a finger or other object) by detecting changes over time in the temperature detected using the substrate sensor 355.

The output component 320 could be configured to provide an indication related to a variety of different types of information via a variety of means. The output component 320 could provide an indication related to the operational state of the sensing platform 300 (e.g., related to a battery charge state or free memory space of the device) and/or related to a physiological property detected using one or both of the sensors 355, 362 (e.g., related to a blood glucose level detected using the probe sensor 362). The output component 320 could be used to provide an indication related to a course of action that a user could take (e.g., to administer a drug, to seek medical assistance). The output component 320 could be used to provide an indication of some alert generated by the sensing platform 300 (e.g., an alert that a measured physiological property is outside of specified limits, and alert that a user is experiencing an adverse health state). The output component 320 could include light-emitting elements (e.g., LEDs, OLEDs, displays), color-changing elements (e.g., e-ink elements or displays, LCDs), haptic elements (e.g., vibrators, buzzers, electrohaptic elements), acoustical elements (e.g., buzzers, speakers), or some other elements configured to provide an indication of some information, e.g., to a user. The input 310 and/or output 320 components could include flexible elements, e.g., the output component 320 could include a flexible OLED display.

The sensor interface module 352 and connections 351 between the sensor interface module 352 and the sensors 355, 362 could take a variety of forms according to the methods used to detect a physiological property (e.g., an analyte in interstitial fluid to which the probe sensor 362 is exposed). One or both of the sensors 355, 362 can include an analyte-selective substance that selectively interacts with the analyte in a fluid (e.g., interstitial fluid in skin, sweat on the surface of the skin). The analyte-selective substance can include proteins, enzymes, reagents, ionophores, antibodies, fluorophores, nano-structured surfaces and/or structures, or other substances that selectively bind to, react with, change one or more properties in response to the presence of, or otherwise selectively interact with the analyte. The sensor(s) 355, 362 and sensor interface 352 can then detect the selective interaction between the analyte and the analyte-selective substance to detect a presence, concentration, or other properties of the analyte.

Such detection can include detecting the interaction between the analyte and the analyte-selective substance directly (e.g., by detecting a change in an optical property of the analyte-selective substance in response to interaction with the analyte, by detecting a change in electrical potentials at the sensor(s) 355, 362 due to accumulation of a charged analyte by the analyte-selective substance) or indirectly (e.g., by detecting a reaction product of the selective reaction of the analyte, e.g., by detecting hydrogen peroxide produced by oxidation of the analyte by the analyte-selective substance). Direct or indirect detection of the analyte could include electrochemical detection (i.e., the sensor could include two or more electrodes configured to electrochemically detect the analyte), optical detection (i.e., the sensor(s) 355, 362 and/or the sensor interface 352 could include a light emitter and/or light detector configured to detect an optical property of the analyte and/or the analyte-selective substance that is related to the presence, concentration, or some other property of the analyte), or some other detection means.

In some examples, one or both of the sensors 355, 362 include at least a reference electrode and a working electrode. The working electrode is selectively sensitive to an analyte of interest, for example, by having an analyte-selective substance localized proximate to the working electrode (e.g., by being disposed on a surface of the working electrode, by being disposed in an analyte-permeable polymer layer disposed on the working electrode). The sensor interface 352 is configured to operate the sensor(s) 355, 362 to electrochemically detect the analyte.

In some examples, one or both of the sensors 355, 362 can be a potentiometric sensor. In such examples, a voltage can develop between the working and reference electrodes related to a concentration of analyte in a fluid to which the working electrode is exposed. Thus, the sensor interface 352 can measure a magnitude of the potentiometric voltage between the working electrode and the reference electrode to provide an indication of analyte concentration. In such embodiments, the sensor interface 352 can include a high-impedance voltmeter configured to measure the voltage difference between working and reference electrodes while substantially preventing the flow of current through the working and reference electrodes.

Additionally or alternatively, one or both of the sensors 355, 362 can be an amperometric sensor. In such examples, the sensor interface 352 can apply a specified voltage between the reference electrode and the working electrode. The applied voltage can drive an electrochemical current through the working electrode that is related to the concentration of an analyte near the working electrode. Such an electrochemical current can be related to redox or other reactions of the analyte at the surface of the working electrode and/or could be related to redox or other reactions of reaction products of the analyte at the surface of the working electrode (e.g., reaction products produced by reaction of the analyte due to selective interaction with the analyte-selective substance). Thus, the sensor interface 352 can measure a magnitude of the amperometric current passing through the working electrode to provide an indication of analyte concentration. In such embodiments, the sensor interface 352 can include a specified voltage source (to provide the specified voltage between the reference electrode and the working electrode) and a current meter configured to measure the current passing through the working electrode due to the applied specified voltage. In some examples, one or both of the sensors 355, 362 could additionally include a counter electrode through which a return current (i.e. a current having a magnitude substantially equal but opposite to the current passing through the working electrode) could pass, such that substantially no current passes through the reference electrode. Such an embodiment could allow for the reference electrode to provide a more stable voltage relative to the fluid to which one or both of the sensors 355, 362 are exposed.

In some examples, one or both of the sensors 355, 362 could include an analyte-selective substance that has an optical property that is related to the presence, concentration, or some other property of the analyte. For example, the substance could include a fluorophore having a fluorescence intensity, a fluorescence lifetime, an emission wavelength, an excitation wavelength, or some other property that is related to the analyte. In some examples, such an analyte-selective substance could include a protein or other element configured to selectively bind to the analyte and to experience a conformation change in response to such binding. A fluorophore and a quencher could be attached to the protein such that the distance between the fluorophore and the quencher is related to whether the protein is bound to the analyte; as a result, the degree of fluorescence of the fluorophore could be related to whether the protein is bound to the analyte. Additionally or alternatively, a color, saturation, absorption spectrum, or some other optical property of a substance disposed at the end of the sensor probe could be related to the presence, concentration, or some other property of the analyte.

In such examples, the sensor interface 352 and/or one or both of the sensors 355, 362 could include a light emitter and/or a light detector configured to illuminate and/or to receive light emitted from the analyte-sensitive substance, respectively, in order to determine the optical property of the substance that is related to the analyte. In some examples, the light emitter and/or light detector could be disposed as part of the probe sensor 362 (i.e., disposed on the sensor probe 360) and connected to the sensor interface 352 via conductive interconnects (e.g., the sensor interconnect 351 could include traces patterned or otherwise disposed on the sensor probe 360). Additionally or alternatively, the sensor probe 360 could include an optical fiber and the analyte-selective substance could be disposed on a distal end of such an optical fiber. In such examples, the light emitter and/or a light detector could be disposed at a proximal end of the optical fiber (e.g., on the flexible substrate 330 as part of the sensor interface 352), such that the light emitter and light detector illuminate and/or receive light from the analyte-sensitive substance via the optical fiber.

The memory 354 could include a variety of volatile and nonvolatile electronic storage elements configured to provide means for the sensing platform 300 to record and/or log detected information about the analyte (e.g., concentrations measured using the sensor 362 at a plurality of points in time) and/or other information detected by or input to (e.g., via the input component 310) the sensing platform 300. For example, the memory 354 could include one or more EEPROM memories, flash memories, NVRAM memories, DRAM memories, SRAM memories, flip-flops, or other information storage elements. The memory 354 could have an information storage capacity sufficient to record some specified period of detected information at some specified rate of detection; e.g., the memory 354 could have a capacity sufficient to record more than 18 hours, a week, or some other protracted period of time of detected information (e.g., concentrations of an analyte) when detected at a rate of approximately once per minute. Additionally or alternatively, the sensing platform 300 could be in communication with a memory that is external to the sensing platform 300 and that could be used as described above (e.g., to store physiological property measurement data, to store and/or access calibration or other configuration data of the sensing platform 300).

The electronics 350 include a communication circuit 356 for sending and/or receiving information via the antenna 370. The communication circuit 356 can optionally include one or more oscillators, mixers, frequency injectors, etc. to modulate and/or demodulate information on a carrier frequency to be transmitted and/or received by the antenna 370. In some examples, the body-mountable sensing platform 300 is configured to indicate information (e.g., detected analyte concentrations using the probe sensor 362) by modulating an impedance of the antenna 370 in a manner that is perceivably by the external reader 380. For example, the communication circuit 356 can cause variations in the amplitude, phase, and/or frequency of backscatter radiation from the antenna 370, and such variations can be detected by the reader 380. Such wireless communication could be compatible with one or more existing backscatter wireless communications standards, e.g., RFID. Additionally or alternatively, the communication circuit 356 and antenna 370 could be configured to transmit wireless signals according to some other method, e.g., according to the Bluetooth (e.g., Bluetooth Low Energy), ZigBee, WiFi, LTE, and/or some other wireless communications standard or scheme. In some examples, such communications (e.g., data transmitted from the sensor platform 300, operational instructions transmitted to the sensor platform 300) could be cryptographically secured; that is, the wireless communications link could be encrypted.

The sensor interface 352 is connected to the sensor(s) 355, 362 via sensor interconnects 351. In some examples, the sensor interconnects 351 could include a patterned conductive material (e.g., gold, platinum, palladium, titanium, copper, aluminum, silver, metals, combinations of these, etc.) to connect electrodes, light emitters, light detectors, or other components of the sensor(s) 355, 362 to a terminal on a microcontroller or other component(s) comprising the sensor interface 352. Similarly, the electronics 350 are connected to the antenna 370 via interconnects 357. Additionally or alternatively, the sensor interconnects 351 could include an optical fiber or other means for transmitting light between the sensor(s) 355, 362 and the sensor interface 352. For example, the sensor interface 352 could comprise a light emitter and/or light detector and the sensor(s) 355, 362 could include an analyte-sensitive substance that has an optical property that is related to the presence, concentration, or some other property of the analyte. In such examples, the light emitter and/or a light detector could be disposed at a proximal end of the optical fiber, such that the light emitter and light detector illuminate and receive light from the analyte-sensitive substance via the optical fiber of the sensor interconnects 351. Other configurations of the sensor interconnects 351 are anticipated (e.g., capillary tubes, microfluidic elements, etc.).

It is noted that the block diagram shown in FIG. 3 is described in connection with functional modules for convenience in description. However, embodiments of the body-mountable sensing platform 300 can be arranged with one or more of the functional modules ("sub-systems") implemented in a single chip, integrated circuit, and/or physical feature or on multiple such elements.

The external reader 380 includes an antenna 388 (or group of more than one antenna) to send and receive wireless signals 371 to and from the body-mountable sensing platform 300. The external reader 380 also includes a computing system with a processor 386 in communication with a memory 382. The external reader 380 can also include one or more of user controls 385, a display 387, and a communication interface 389. The memory 382 is a non-transitory computer-readable medium that can include, without limitation, magnetic disks, optical disks, organic memory, and/or any other volatile (e.g. RAM) or non-volatile (e.g. ROM) storage system readable by the processor 386. The memory 382 can include a data storage 383 to store indications of data, such as sensor readings (e.g., acquired using the sensors 355, 362), program settings (e.g., to adjust behavior of the body-mountable sensing platform 300 and/or external reader 380), etc. The memory 382 can also include program instructions 384 for execution by the processor 386 to cause the external reader 380 to perform processes specified by the instructions 384. For example, the program instructions 384 can cause external reader 380 to perform any of the function described herein. For example, program instructions 384 may cause the external reader 380 to provide a user interface that allows for retrieving information communicated from the body-mountable sensing platform 300 (e.g., sensor outputs from the sensors 355, 362) by displaying that information on the display 387 in response to commands input through the user controls 385. The external reader 380 can also include one or more hardware components for operating the antenna 388 to send and receive the wireless signals 371 to and from the body-mountable sensing platform 300. For example, oscillators, frequency injectors, encoders, decoders, amplifiers, filters, etc. can drive the antenna 388 according to instructions from the processor 386.

The external reader 380 can also be configured to include a communication interface 389 to communicate signals via a communication medium 391 to and from a remote system 390. For example, the remote system 390 may be a smart phone, tablet computer, laptop computer, or personal computer, and communication interface 389 and communication medium 391 may be a Bluetooth module and wireless Bluetooth communication signals, respectively. In this example, the external reader 380 may be configured to send information about measured physiological properties collected using the sensor(s) 355, 362 to the smart phone, tablet computer, laptop computer, or personal computer for storage and offline analysis. In another example, the remote system 390 is a server at a clinic or physician's office, the communication interface 389 is a WiFi radio module, and the communication medium 391 is elements of the internet sufficient to enable the transfer of data between the remote server and the WiFi radio module. A physician may use this data to make determinations or diagnoses related to the subject's condition. Further, the external reader 380 may be configured to receive signals from a remote server, such as instructions sent by a physician at a remote location to, for example, increase or decrease sampling frequency. Communication interface 389 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 380 can be a smart phone, digital assistant, or other portable computing device with wireless connectivity sufficient to provide the wireless communication link 371. The external reader 380 can also be implemented as an antenna module that can be plugged in to a portable computing device, such as in an example where the communication link 371 operates at carrier frequencies not commonly employed in portable computing devices. In some instances, the external reader 380 is a special-purpose device configured to be periodically placed relatively near the sensing platform 300 to allow the wireless communication link 371 to operate with a low power budget.

In some examples, the sensor(s) 355, 362 could be configured to detect glucose in the body of a person and the external reader 380 could include or be in contact with an insulin pump. Such an insulin pump could include a supply of insulin and a pump configured to provide the insulin, at a controlled rate, into the body of the person (e.g., through a tube placed in and/or through the skin of the body of the person using, e.g., a needle). In such examples, the insulin pump could be operated based on measurements of glucose levels (e.g., concentrations) in the body of the person detected using the sensor(s) 355, 362. For example, the insulin pump could be operated to provide insulin at a rate based on the detected glucose levels such that the blood glucose levels of the person are maintained within a specified range, or according to some other scheme (e.g., the insulin pump could be operated as part of a feedback loop that includes the sensor(s) 355, 362). Additionally or alternatively, the external reader 380 could include or be in contact with a pump for some other pharmaceutical and could be operated to provide that pharmaceutical at a controlled rate based on a detected level of glucose or of some other analyte or physiological property detected using the sensor(s) 355, 362.

In an example where the body-mountable sensing platform 300 has been mounted to skin of a living body such that the probe 362 is in contact with interstitial fluid of the living body, the sensing platform 300 can be operated to detect an analyte (e.g., to measure a concentration of the analyte) in the interstitial fluid. Interstitial fluid is an extravascular fluid that suffuses many of the tissues of a living animal body. The interstitial fluid is continuously replenished by the blood supply through capillaries in the structure of tissue (e.g., dermal tissue, subcutaneous tissue) and includes many biomarkers found in blood that are analyzed to characterize a person's health condition(s). For example, the interstitial fluid includes urea, glucose, calcium, sodium, cholesterol, potassium, phosphate, other biomarkers, etc. The biomarker concentrations in the interstitial can be systematically related to the corresponding concentrations of the biomarkers in the blood, and a relationship between the two concentration levels can be established to map interstitial fluid biomarker concentration values to blood concentration levels. Thus, measuring interstitial fluid analyte concentration levels using sensing platforms as described herein can provide a technique for monitoring analyte levels in comparison to blood sampling techniques performed by lancing a volume of blood to be analyzed outside a person's body. Moreover, the body-mountable sensor platform disclosed here can be operated substantially continuously to enable real time measurement of analyte concentrations or other information about an analyte.

In some embodiments, the body-mountable sensing platform 300 can operate to non-continuously ("intermittently") indicate information related to a physiological property (e.g., concentration values of an analyte in interstitial or other fluids). For example, the body-mountable sensing platform 300 could operate to periodically operate the probe sensor 362 to detect an analyte and to store information related to the detection of the analyte in the memory 354. The sensing platform 300 could then less frequently operate to transmit stored information relating to more than one detection of the analyte or other physiological property. Additionally or alternatively, a user could operate the external reader 380 to request such information transmission by the sensing platform 300. In another example, the sensing platform 300 could provide an indication to a user (e.g., via a light, vibration motor, or other user interface element(s) of the output component 320) that the user should operate the external reader 380 to receive such transmitted information from the sensing platform (e.g., due to the memory 354 being nearly full, due to a battery of the power supply 340 being nearly depleted). Other operations of the systems shown to continuously, periodically, and/or intermittently use the sensor(s) 355, 362 to detect physiological properties, use the memory 354 to store information related to the detected physiological properties, to sue the output component 320 to indicate such information, and/or use the antenna 370 to wirelessly indicate such information are anticipated.

IV. Example User Interactions with a Flexible Biosensor Platform

User interfaces (e.g., input components and/or output components) of a body-mountable sensing platform (e.g., 100, 200, 300) could include a variety of components configured in a variety of ways to receive a variety of inputs and/or to provide an indication related to a variety of types of information. Input components of such a body-mountable sensing platform could be configured and/or operated to receive inputs (e.g., from a user) including the presence of, location of, motion of (e.g., a direction and/or speed of motion), force exerted by, or some other property of a finger, body part, or other object proximate to the input component.

The body-mountable sensing platform could perform a variety of operations based on and/or responsive to one or more such received inputs, including changing an operational state of the sensing platform, initiating a measurement (e.g., of a physiological property) using sensor(s) of the sensing platform, operating an output component to provide an indication related to some information (e.g., a value of a measured property, an operational state of the sensing platform, a battery charge status of the sensing platform), wirelessly linking the sensing platform with a remote system (e.g., a cellphone), transferring information (e.g., recorded and/or logged physiological properties detected using sensor (s) of the sensing platform) from the sensor platform to such a remote system, or some other operations. In some examples, an input component could be used to receive information about events (e.g., activities performed by a user, a drug delivered to the user), a state of a user (e.g., an emotional state, a physical state, a degree of pain experienced), operational parameters or settings of the sensing platform (e.g., calibration data describing a relationship between values of a property detected by a sensor of the sensing platform and true and/or baseline values of the detected property), or other information.

A body-mountable sensing platform could include a touch-sensitive display (e.g., as in FIG. 1A) configured to receive inputs that include the presence, location, motion, or other properties of one or more fingers, body parts, or other objects proximate the sensing platform (e.g., by detecting the capacitance of and/or proximate to the touch-sensitive display) and to provide an indication related to some information by presenting images on a multipixel display (e.g., a flexible, multipixel OLED display). However, body-mountable sensing platforms are anticipated that include different and/or differently operated and/or operated input and output components and/or that omit output means entirely.

Figure 4A:
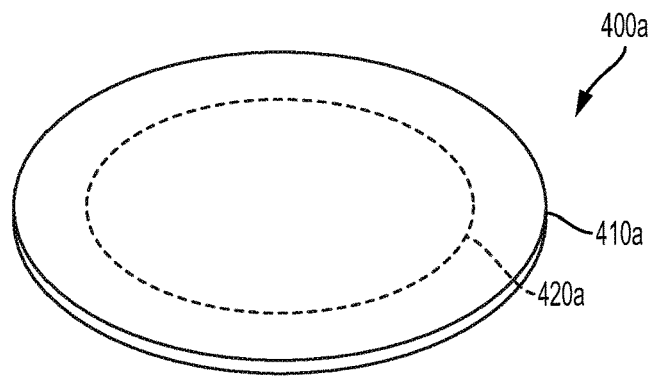
FIG. 4A is a top aspect view of an example body-mountable device.

In an example, FIG. 4A illustrates a flexible, body-mountable sensing platform 400a that includes a flexible substrate 410a configured to be mounted to a skin surface. Sensors, electronics, batteries, and/or other components could be disposed on or within the flexible substrate 410a to provide functions of the sensing platform 400a (e.g., detection of one or more physiological properties of skin to which the sensing platform 400a is mounted, e.g., a concentration of an analyte in interstitial fluid within the skin). The sensing platform 400a additionally includes an input component configured to detect that a finger, body part, or other object is proximate to and/or is contacting the illustrated region 420a of the sensing platform 400a. Such detected proximity and/or contact could comprise inputs received by the sensing platform 400a. The sensing platform could record such received inputs (e.g., a user could press and/or contact the sensing platform with a finger to indicate an event, e.g., that the user has eaten a meal), could change an operational state based on such inputs, or could perform some other functions based on and/or responsive to such inputs.

The sensitive region 420a of the sensing platform 400a could correspond to the location and/or shape of an electrode or other touch-sensing element(s) of an input component (e.g., a capacitive touch sensor, a resistive touch sensor, a conductive touch sensor, a pressure sensor, an ambient light sensor) of the sensing platform 400a. Additionally or alternatively, the input component could be configured to detect the presence, location, motion, direction of motion, or other properties of fingers, body parts, or other objects that are proximate to and/or in contact with the sensing platform 400a. The sensing platform 400a could be configured to determine when a finger or other object contacts the sensitive region 420a based on such detected properties; detecting the properties of the finger or other object and determining that the finger or other object is in contact with the sensitive region 420a could comprise the sensing platform 400a receiving an input (e.g., from a user).

Figure 4B:
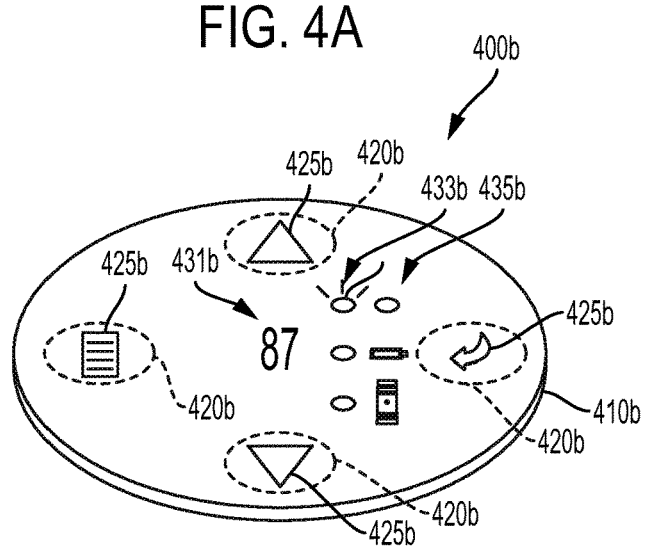
FIG. 4B is a top aspect view of an example body-mountable device.

A body-mountable sensing platform could additionally include an output component configured to provide an indication related to some information. FIG. 4B shows an example body-mountable sensing platform 400b that includes a flexible substrate 410b configured to be mounted to a skin surface. Sensors, electronics, batteries, and/or other components could be disposed on or within the flexible substrate 410b to provide functions of the sensing platform 400b (e.g., detection of one or more physiological properties of skin to which the sensing platform 400b is mounted, e.g., a concentration of an analyte in interstitial fluid within the skin). The sensing platform 400b includes an input component configured to detect that a finger, body part, or other object is proximate to and/or is contacting one or more of the illustrated regions 420b of the sensing platform 400b. The sensing platform 400b additionally includes output components configured to provide an indication related to some information. The output components of the sensing platform 400b include a numeric output 431b configured to indicate numerals (e.g., to provide an indication related to the value of a physiological property detected by a sensor of the sensing platform 400b, to provide an indication related to a setting of an operational parameter of the sensing platform 400b) and a number of light emitters 433b configured to provide an indication by being illuminated.

The sensing platform 400b additionally includes static symbols 425b, 435b printed, etched, embossed, deposited, or otherwise formed on the flexible substrate 410b. A first set 425b of the static symbols indicate regions 420b of the sensing device 400b that can be interacted with (e.g., by contacting with a finger or other object) to present an input to the sensing platform 400b. The first set 425b additionally provide context for the operations that the sensing platform 400b could perform in response to such input, e.g., to increase or decrease an operational parameter (e.g., calibration data) of the sensing platform 400b, to change an operational state of the sensing platform, to navigate a user interface menu of the sensing platform 400b, or to perform some other functions. A second set 435b of the static symbols provide context for the information indicated by respective light emitters of the light emitters 433b, e.g., that the top light emitter emitting light indicates that the sensing platform 400b is operating to periodically record one or more physiological properties (e.g., analyte concentration values in interstitial fluid of skin). The second set of static symbols 435b further provides context that the middle light emitter emitting light indicates that a battery of the sensing platform 400b is nearly discharged and that the bottom light emitter emitting light indicates that a memory of the sensing platform 400b is nearly full (e.g., full of information related to previously obtained sensor readings). Additionally or alternatively, the static symbols 425b, 435b could be presented by a display of the sensing platform 400b.

Figure 4C:
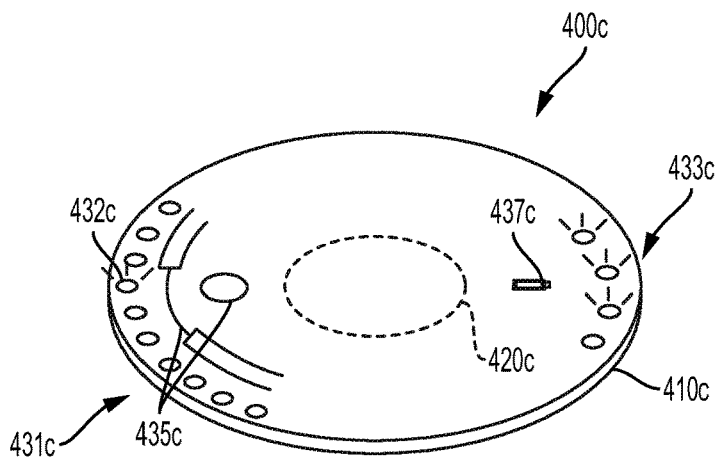
FIG. 4C is a top aspect view of an example body-mountable device.

FIG. 4C shows another example body-mountable sensing platform 400c that includes a flexible substrate 410c configured to be mounted to a skin surface. Sensors, electronics, batteries, and/or other components could be disposed on or within the flexible substrate 410c to provide functions of the sensing platform 400c (e.g., detection of one or more physiological properties of skin to which the sensing platform 400c is mounted, e.g., a concentration of an analyte in interstitial fluid within the skin). The sensing platform 400c includes an input component configured to detect that a finger, body part, or other object is proximate to and/or is contacting the illustrated region 420c of the sensing platform 400c. The sensing platform 400c additionally includes output components configured to provide an indication related to some information. The output components of the sensing platform 400c include first 432c and second 433c sets of light emitters configured to provide an indication by being illuminated. First static symbols 435c provide context that the first set of light emitters 432c provide an indication related to a level of glucose in skin detected using a sensor of the sensing platform 400c. The first static symbols 435c further indicate which of the set of light emitters 435c correspond to measured values of blood glucose within a specified range (e.g., a 'safe' range of measured blood glucose, measured values outside of such range indicating hypoglycemia, hyperglycemia, or some other medical condition and/or that a user should administer a drug or perform some other action). Second static symbols 437c provide context that the second set of light emitters 433c provide an indication related to a level of charge of a battery or other power source of the sensing platform 400c. The first 432c and/or second 433c sets of light emitters could be operated to provide an indication in response to an input received by the sensing platform 400c (e.g., in response to detecting that a finger or other object is in contact with the illustrated region 420c).

Body-mountable sensing platforms as described herein could be mounted to skin at a variety of different locations of a body. Such locations could be selected to provide access to a particular portion of skin and/or a particular type or portion of tissue (e.g., to provide access to a portion of subsurface vasculature). Additionally or alternatively, such locations could be selected to minimize discomfort caused by the sensing platform being mounting to skin for a protracted period of time (e.g., by being mounted to a portion of skin that includes fewer nerve endings and/or that is minimally strained during the performance of activities of daily living). Further, where a sensing platform includes an input component, an output component, and/or some other user interface means, such locations could be selected to provide convenient interaction between a wearer and the user interface (e.g., locations that allow easy contact between a finger of a user and the sensing platform, location that allow easy viewing of visually-indicating output components of the sensing platform). Such locations could include locations on the arms or abdomen of a user.

Figure 5:
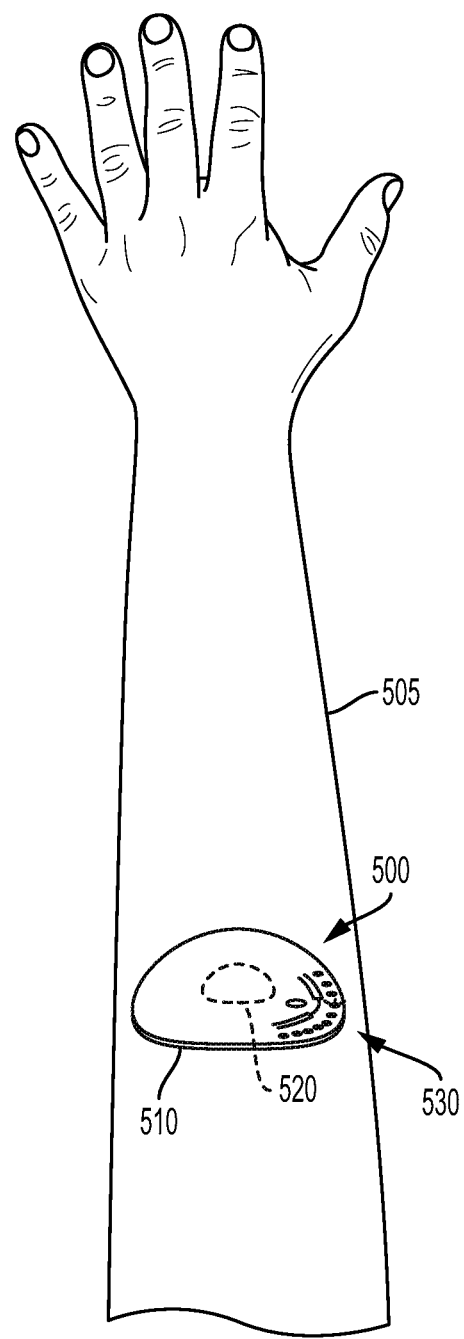
FIG. 5 is an aspect view of an example body-mountable device mounted to a body.

FIG. 5 illustrates such a location, showing a body-mountable sensing platform 500 mounted to skin of an arm 505.

The body-mountable sensing platform 500 includes a flexible substrate 510 configured to be mounted to a skin surface of the forearm of the arm 505. Sensors, electronics, batteries, and/or other components could be disposed on or within the flexible substrate 510 to provide functions of the sensing platform 500 (e.g., detection of one or more physiological properties of skin to which the sensing platform 500 is mounted, e.g., a concentration of an analyte in interstitial fluid within the skin). The sensing platform 500 includes an input component configured to detect that a finger, body part, or other object is proximate to and/or is contacting the illustrated region 520 of the sensing platform 500. The sensing platform 500 additionally includes output components 530 configured to provide an indication related to some information (e.g., an indication related to values of physiological properties detected by sensor(s) of the sensing platform 500). Note that the flexible substrate 510, and the sensing platform as a whole 500, are sufficiently flexible that the sensing platform 500 deforms (i.e., curves) according to the surface of the skin to which the flexible substrate 510 is mounted. This could include the input component 520, output component 530, and/or other components (e.g., electronics, sensors) being sufficiently flexible to deform according to the surface of the skin. Additionally or alternatively, one or more components of the sensing platform 500 could be rigid and shaped and/or sized such that, when disposed on the flexible substrate 510, the sensing platform 500 as a whole deforms according to the surface of the skin to which the flexible substrate 510 is mounted.

The particular body-mountable sensing platforms, input components, output components, user interfaces, and configurations and operations thereof illustrated herein (e.g., as body-mountable sensing platforms 100, 200, 300, 400*a*, 400*b*, 400*c*, 500) are intended as non-limiting examples. Differently-configured sensing platforms (e.g., having differently-shaped and/or sized flexible substrates or other components), input and/or output components, or other properties of the configuration and operation of body-mountable sensing platforms are anticipated, as will be clear to one of skill in the art.

V. Example Methods

Figure 6:
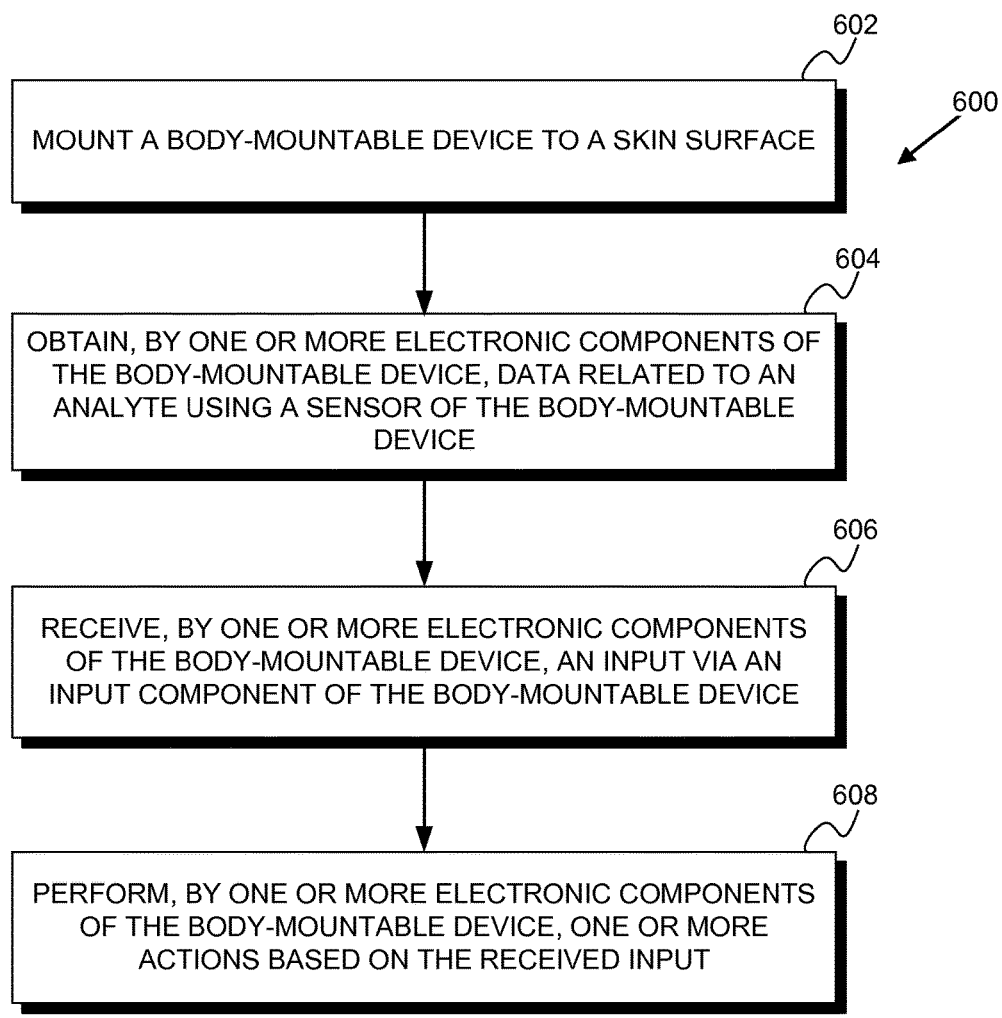
FIG. 6 is a flowchart of an example method.

FIG. 6 is a flowchart of a method 600 for a body-mountable device. The body-mountable device includes (i) a flexible substrate, (ii) a sensor probe that has a first end attached to the flexible substrate and a second end that is configured to extend beneath the skin surface to contact interstitial fluid, (iii) a sensor disposed at the second end of the sensor probe and configured to detect an analyte in the interstitial fluid, (iv) one or more electronic components disposed on the substrate, and (v) an input component disposed on the flexible substrate.

The method 600 includes mounting the body-mountable device to the skin surface (602). Mounting the body-mountable device to the skin surface (602) could include using an adhesive layer of the body-mountable device to mount the flexible substrate to the skin surface. Additionally or alternatively, a liquid adhesive, tape, strap, dry adhesive, or other means could be used to mount the flexible substrate to the skin surface. Further, mounting the body-mountable device to the skin surface (602) could include installing the sensor probe in the skin such that the sensor probe penetrates the skin and further such that the sensor disposed on the sensor probe is placed in contact with a fluid (e.g., interstitial fluid) within the skin. This could include placing the sensor probe in a puncture, cut, or other incision that has been formed in the skin (e.g., by a needle, a lancet, a scalpel, or by some other means). Alternatively, the sensor probe could be configured to penetrate and/or pierce the skin (e.g., by being sharpened and/or having a sufficiently high rigidity).

The method 600 additionally includes obtaining, by one or more of the electronic components of the body-mountable device, data related to the analyte using the sensor (604). In some examples, the sensor could be a potentiometric electrochemical sensor, and obtaining analyte data (604) could include measuring a voltage between two or more electrodes. In some examples, the sensor could be an amperometric electrochemical sensor, and obtaining analyte data (604) could include applying a specified voltage between two or more electrodes and measuring a current through one of the two or more electrodes. In some examples, the sensor could be an optical sensor, and obtaining analyte data (604) could include illuminating and/or detecting light emitted from a substance that is in contact with a fluid and that has one or more optical properties related to the analyte in the fluid.

Obtaining analyte data (604) could include determining a concentration of the analyte in a fluid, determining that the analyte is present in the fluid (e.g., that the concentration of the analyte in the fluid is above some threshold), determining that the concentration of the analyte is within some specified range of concentrations, determining a state of the analyte (e.g., determining a distribution of isoforms and/or conformational states of the analyte in the fluid), or determining some other information about the analyte. Obtaining analyte data (604) could include determining a concentration or other information about the analyte at a plurality of different points in time (e.g., at a specified rate). Obtaining analyte data (604) could include determining a concentration or other information about the analyte based on calibration data stored by, input into, or otherwise accessible by the sensing platform (e.g., based on calibration data that describes a relationship between a value of a property (e.g., a voltage, a current) measured by the sensor and a corresponding value of the analyte, e.g., concentration of the analyte). Obtaining analyte data (604) could be performed in response to a request for such data (e.g., by an external system in communication with the body-mountable device).

The method 600 additionally includes receiving, by one or more of the electronic components of the body-mountable device, an input via the input component (606). Receiving an input (606) could include detecting the presence, location, motion, direction of motion, or other properties of one or more fingers, body parts, or other objects proximate to and/or in contact with the input component. Detecting such information could include operating a temperature sensor, capacitive touch sensor, pressure sensor, resistive touch sensor, light sensor, or other sensor(s). In some examples, receiving an input (606) could include using one or more elements of the sensor to detect a property of the sensing platform and/or of the environment of the sensing platform. Receiving an input (606) could include detecting a location, orientation, motion, temperature, or other information about the sensing platform. Receiving an input (606) could include making a determination based on detected information about the sensing platform, about the environment of the sensing platform, about a finger, body part, or other object proximate to the input component. For example, a detected location and/or presence of a finger could be used to determine that the finger is in contact with a specified region of the sensing platform, and the detecting in combination with the determination could comprise receiving an input.

The method 600 further includes performing, by one or more of the electronic components of the body-mountable device, one or more actions based on the received input (608). This could include changing an operational state of the sensing platform (e.g., a sleep state, a data logging state) based on the received input. In some examples, the one or more actions could include obtaining analyte data (604); that is, the analyte data could be obtained responsive to the received input (e.g., a user could provide an input to the sensing platform to initiate a sensing period that includes operating the sensor to obtain analyte data). The one or more actions could include operating an output component of the sensing platform (e.g., a display, a haptic element, a vibrator) to provide an indication related to some information (e.g., to provide an indication related to the analyte, to provide an indication related to an alert state determined by the sensing platform) to a user.

In some examples, the method 600 could include receiving, via the input component, calibration information about the operation of the sensor. This could include determining, based on the received input, a calibration value of the analyte in the interstitial fluid. Such a calibration value could be generated, e.g., by another sensing device (e.g., a lancet and handheld glucose meter, in examples wherein the analyte is glucose), measured value of the analyte in the interstitial fluid (or of the analyte in some other related fluid). Calibration data could then be determined for the sensor based on the calibration value and further based on the data related to the analyte obtained using the sensor (e.g., an electrochemical potential and/or current measured by an electrochemical sensor). The method 600 could further include obtaining subsequent data related to the analyte using the sensor (e.g., operating the sensor a further time to generate further information about the analyte in the interstitial fluid). A property of the analyte in the interstitial fluid (e.g., a concentration in the interstitial fluid) could be determined based on the determined calibration data and further based on the subsequent data related to that analyte that was obtained using the sensor.

The method 600 could include additional steps. For example, the method 600 could include using a memory of the device to store information relating to the analyte (e.g., detected analyte concentration values). The method 600 could include wirelessly transmitting information relating to the analyte. The method 600 could include determining a health state, a course of treatment, a dose and/or timing of administration of a drug, or some other information based on detected analyte data. The method 600 could include provide an indication related to detected analyte data, determined dosing and/or timing of administration of a drug, or some other information generated by and/or available to the device using an output component of the device (e.g., LEDs, displays, vibrators, haptic elements) and/or via a user interface of an external device in communication with the device. The method 600 could include determining an alert state based on the obtained analyte data, e.g., determining that a user is experiencing a medical condition, that a detected physiological parameter (e.g., an analyte concentration) is outside of a specified range of values, that a user could seek medical attention, that a user should receive a drug, or an alert corresponding to some other information.

Additional and/or alternative steps, or alternative embodiments of the listed steps, are anticipated.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A body-mountable device comprising:
   a flexible substrate, wherein the flexible substrate has a first side and a second side opposite the first side, wherein the first side of the flexible substrate comprises an adhesive configured to adhere the flexible substrate to a skin surface;
   a sensor coupled to the first side of the flexible substrate, wherein the sensor is configured to detect a physiological property;
   an input component disposed on the second side of the flexible substrate, wherein the input component comprises a further sensor, wherein the input component is flexible such that the input component curves according to the skin surface to which the flexible substrate is adhered, and wherein the input component comprises an electrode directly formed on the second side of the flexible substrate; and
   one or more electronic components, disposed on the flexible substrate, configured to: (i) use the sensor to obtain data related to the physiological property; (ii) use the input component to receive an input, wherein operating the input component to receive an input comprises (a) operating the further sensor to detect a physical variable and (b) detecting a change in the detected physical variable; and (iii) perform one or more actions based on the received input.

2. The body-mountable device of claim 1, wherein the electrode is configured as a capacitive touch sensor.

3. The body-mountable device of claim 1, wherein the input component comprises a temperature sensor.

4. The body-mountable device of claim 1, wherein the input component comprises a pressure sensor.

5. The body-mountable device of claim 1, further comprising a flexible display disposed on the flexible substrate, and wherein the one or more electronic components are further configured to use the display to provide an indication related to the physiological property.

6. The body-mountable device of claim 1, further comprising a haptic device, and wherein the one or more electronic components are further configured to use the haptic device to provide an indication related to the physiological property.

7. The body-mountable device of claim 1, further comprising an acoustical element, and wherein the one or more electronic components are further configured to use the acoustical element to provide an indication related to the physiological property by generating a sound.

8. The body-mountable device of claim 1, further comprising:
a sensor probe, wherein a first end of the sensor probe is attached to the first side of the flexible substrate, wherein a second end of the sensor probe is configured to extend beneath the skin surface to contact interstitial fluid, wherein the sensor is disposed at the second end of the sensor probe, and wherein the physiological property comprises a property of an analyte in the interstitial fluid.

9. The body-mountable device of claim 1, further comprising:
an output component, wherein the output component is disposed on the flexible substrate, and wherein the processor is further programmed to operate the output component to provide an indication in response to the received input.

10. The body-mountable device of claim 1, wherein the input component comprises an ambient light sensor.

11. The body-mountable device of claim 1, wherein the one or more electronic components are further configured to: (iv) determine a calibration value of the physiological property based on the received input; (v) determine calibration data for the sensor based on the calibration value and the data related to the physiological property; (vi) operate the sensor to obtain subsequent data related to the physiological property; and (vii) determine a property of the physiological property based on the determined calibration data and the subsequent data related to the physiological property.

12. A method comprising:
operating a body-mountable device mounted to a skin surface, wherein the body mountable device comprises:
a flexible substrate, wherein the flexible substrate has a first side and a second side opposite the first side, wherein the first side of the flexible substrate comprises an adhesive configured to adhere the flexible substrate to a skin surface;
a sensor coupled to the first side of the flexible substrate, wherein the sensor is configured to detect a physiological property;
one or more electronic components disposed on the flexible substrate; and
an input component disposed on the second side of the flexible substrate, wherein the input component comprises a further sensor, wherein the input component is flexible such that the input component curves according to the skin surface to which the flexible substrate is adhered, and wherein the input component comprises an electrode directly formed on the second side of the flexible substrate; wherein the operating comprises:
obtaining, by the one more electronic components, data related to the physiological property using the sensor;
receiving, by the one more electronic components, an input via the input component, wherein receiving an input via the input component comprises (i) operating the further sensor to detect a physical variable and (ii) detecting a change in the detected physical variable; and
performing, by the one more electronic components, one or more actions based on the received input.

13. The method of claim 12, wherein obtaining data related to the physiological property using the sensor is performed in response to the received input.

14. The method of claim 12, wherein the electrode is configured as a capacitive touch sensor, wherein receiving an input via the input component comprises detecting a direction of motion proximate the capacitive touch sensor using the input component.

15. The method of claim 12, further comprising:
determining, by the one or more electronic components, a calibration value of the physiological property based on the received input;
determining, by the one or more electronic components, calibration data for the sensor based on the calibration value and the data related to the physiological property obtained using the sensor;
obtaining, by the one or more electronic components, subsequent data related to the physiological property using the sensor;
determining, by the one or more electronic components, a property of the physiological property based on the determined calibration data and the subsequent data related to the physiological property obtained using the sensor.

16. The method of claim 12, wherein the body-mountable device further comprises an output component, wherein the output component is disposed on the flexible substrate, and further comprising:
providing, via the output component, an indication related to the physiological property.

17. The method of claim 16, further comprising:
determining, based at least on the data related to the physiological property obtained using the sensor, an alert state, wherein the indication is provided responsive to determining the alert state.

18. The method of claim 12, wherein the body-mountable device is configured to communicate with a remote system, and wherein the operating further comprises communicating with the remote system in response to the received input.

19. The method of claim 12, wherein the body-mountable device further comprises:
a sensor probe, wherein a first end of the sensor probe is attached to the first side of the flexible substrate, wherein a second end of the sensor probe is configured to extend beneath the skin surface to contact interstitial fluid, wherein the sensor is disposed at the second end of the sensor probe, and wherein the physiological property comprises a property of an analyte in the interstitial fluid.

20. The method of claim 12, wherein the one or more actions based on the received input comprise recording information about the received input in a memory.

21. The method of claim 12, wherein the body-mountable device further comprises an output component, wherein the output component is disposed on the flexible substrate, and further comprising:

providing, via the output component, an indication in response to the received input.

* * * * *